(12) United States Patent
Yu et al.

(10) Patent No.: US 10,323,228 B2
(45) Date of Patent: Jun. 18, 2019

(54) DIFFERENTIATION OF HEPATOCYTE-LIKE CELLS FROM STEM CELLS

(71) Applicant: Agency for Science, Technology and Research, Singapore (SG)

(72) Inventors: Hanry Yu, Singapore (SG); Derek Phan, Singapore (SG); Yi-chin Toh, Singapore (SG); Farah Tasnim, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 57 days.

(21) Appl. No.: 15/504,139

(22) PCT Filed: Sep. 17, 2015

(86) PCT No.: PCT/SG2015/050325
§ 371 (c)(1),
(2) Date: Feb. 15, 2017

(87) PCT Pub. No.: WO2016/043666
PCT Pub. Date: Mar. 24, 2016

(65) Prior Publication Data
US 2017/0260503 A1     Sep. 14, 2017

(30) Foreign Application Priority Data
Sep. 19, 2014   (SG) .......................... 10201405916Y

(51) Int. Cl.
*C12N 5/071*       (2010.01)
*G01N 33/50*       (2006.01)

(52) U.S. Cl.
CPC ......... *C12N 5/067* (2013.01); *G01N 33/5014* (2013.01); *G01N 33/5067* (2013.01);
(Continued)

(58) Field of Classification Search
CPC .......................... C12N 2506/02; C12N 5/067; C12N 2501/16; C12N 2501/115; C12N 2501/415; C12N 2501/155; C12N 2501/12; C12N 2501/727; C12N 2501/113; C12N 2501/119; C12N 2501/15; C12N 2501/40; C12N 2501/724; C12N 2501/73; C12N 2501/999; C12N 2500/62; C12N 2506/45; C12N 5/0606; C12N 5/0696; C12N 2501/20; C12N 2501/237; C12N 2501/39; C12N 2501/65; C12N 2506/025; C12N 2506/03; C12N 5/0671; C12N 2500/32; C12N 2501/11; C12N 2501/33; C12N 5/0618; C12N 5/0623; C12N 15/111; C12N 15/1131; C12N 15/1132; C12N 2310/14; C12N 2320/11; C12N 2330/10; C12N 2501/385; C12N 2501/405; C12N 2501/41; C12N 2501/60; C12N 2501/606; C12N 2501/998; C12N 2533/52; C12N 2533/90; C12N 2740/16022; C12N 5/0603; C12N 5/0619; C12N 5/0672; C12N 5/0678; C12N 15/8509; C12N 2503/02; C12N 2506/1384; C12N 2800/90; C12N 2830/008; C12N 2830/80; C12N 5/0068; C12N 5/0657; C12N 5/0667; C12N 9/22; C12N 15/85; G01N 33/5067; G01N 33/5014; G01N 33/5023; A61K 35/407; A61K 35/545; A61K 31/28; A61K 31/714; A61K 38/00; A61K 45/06; C07K 14/005; C07K 2319/09; Y02A 90/26; A01N 1/0226;
(Continued)

(56) References Cited

U.S. PATENT DOCUMENTS 8,178,349 B2 * 5/2012 Terskikh .............. C12N 5/0623
                                                435/325
8,207,316 B1 * 6/2012 Bentwich ............. C07K 14/005
                                                536/23.1
(Continued)

FOREIGN PATENT DOCUMENTS

WO    WO-03/050249 A2    6/2003
WO    WO-2006/034873 A1  4/2006
(Continued)

OTHER PUBLICATIONS

Czysz, K. et al., DMSO Efficiently Down Regulates Pluripotency Genes in Human Embryonic Stem Cells during Definitive Endoderm Derivation and Increases the Proficiency of Hepatic Differentiation, PLOS ONE, 1-16 (Feb. 6, 2015).
(Continued)

*Primary Examiner* — Deborah K Ware
(74) *Attorney, Agent, or Firm* — Choate, Hall & Stewart LLP

(57) ABSTRACT

Disclosed are methods of differentiating stem cells in order to obtain hepatocyte-like cells, the method comprising the steps of a) subjecting definitive endoderm to at least one epigenetic modulator to obtain hepatoblasts and b) subjecting the hepatoblasts to at least one stem cell differentiation pathway inhibitor to obtain hepatocyte-like cells; wherein steps a) and b) do not comprise the use of a growth factor. In one preferred embodiment, the epigenetic modulator may be sodium butyrate and/or DMSO and the stem cell differentiation pathway inhibitor may be SB431542 and/or DMSO. Also disclosed are hepatocyte-like cells obtained from the method and uses of these cells such as drug screening.

15 Claims, 13 Drawing Sheets

(52) U.S. Cl.
CPC ...... *C12N 2500/62* (2013.01); *C12N 2501/15* (2013.01); *C12N 2501/16* (2013.01); *C12N 2501/415* (2013.01); *C12N 2501/724* (2013.01); *C12N 2501/727* (2013.01); *C12N 2501/73* (2013.01); *C12N 2501/999* (2013.01); *C12N 2506/02* (2013.01)

(58) Field of Classification Search
CPC ............ A01K 2217/05; A01K 2227/40; A01K 2267/0393; A01K 67/0275
See application file for complete search history.

(56) References Cited

U.S. PATENT DOCUMENTS

| | | | |
|---|---|---|---|
| 9,057,051 | B2* | 6/2015 | Pauwelyn ............... C12N 5/067 |
| 9,090,878 | B2* | 7/2015 | Sancho-Bru ............ C12N 5/067 |
| 2008/0254004 | A1* | 10/2008 | Terskikh ............... C12N 5/0623 424/93.7 |
| 2010/0062527 | A1 | 3/2010 | Pera et al. |
| 2010/0143313 | A1 | 6/2010 | Yarmush et al. |
| 2011/0287539 | A1* | 11/2011 | Pauwelyn ............... C12N 5/067 435/377 |
| 2012/0009672 | A1* | 1/2012 | Sancho-Bru ............ C12N 5/067 435/353 |
| 2013/0071931 | A1 | 3/2013 | Ishikawa |
| 2014/0186954 | A1* | 7/2014 | Pauwelyn ............... C12N 5/067 435/377 |
| 2015/0175962 | A1 | 6/2015 | Zhu et al. |
| 2015/0329821 | A1* | 11/2015 | Ang ...................... C12N 5/0606 435/366 |

FOREIGN PATENT DOCUMENTS

| | | |
|---|---|---|
| WO | WO-2011/116930 A1 | 9/2011 |
| WO | WO-2013/062140 A1 | 5/2013 |
| WO | WO-2014/124527 A1 | 8/2014 |

OTHER PUBLICATIONS

Allen, J.W. et al., Advances in Bioartificial Liver Devices, Hepatology, 34(3):447-455 (2001).
Aurich, H. et al., Hepatocyte differentiation of mesenchymal stem cells from human adipose tissue in vitro promotes hepatic integration in vivo, Hepatology, 58(4):570-581 (2009).
Bone, H.K. et al., A novel chemically directed route for the generation of definitive endoderm from human embryonic stem cells based on inhibition of GSK-3, Journal of Cell Science, 124(12):1992-2000 (2011).
Borowiak, M. et al., Small molecules efficiently direct endodermal differentiation of mouse and human embryonic stem cells, Cell Stem Cell, 4(4):348-358 (2009).
Cai, J. et al., Directed Differentiation of Human Embryonic Stem Cells into Funcitonal Hepatic Cells, Hepatology, 45(5):1229-1239 (2007).
Castel, J.V. et al., Hepatocyte cell lines: their use, scope and limitations in drug metabolism studies, Expert Opin. Drug Metab. Toxicol., 2(2):183-212 (2006).
Chen, S. et al., Self-renewal of embryonic stem cells by a small molecule, PNAS, 103(46):17266-17271 (2006).
Clotman, F. and Lemaigre, F., Control of Hepatic Differentiation by Activin/TGFβ Signaling, Cell Cycle, 5(2):168-171 (2006).
Clotman, F. et al., Control of liver cell fate decision by a gradient of TGFbeta signaliing modulated by Onecut transcription factors, Genes & Development, 19:1849-1854(2005).
D'Amour, K.A. et al., Efficient differentiation of human embryonic stem cells to definitive endoderm, Nature Biotechnology, 23(12):1534-1541 (2005).
D'Amour, K.A. et al., Production of pancreatic hormone-expressing endocrine cells from human embryonic stem cells, Nature Biotechnology, 24(11):1392-1401 (2006).

Dalton, S., Signaling networks in human pluripotent stem cells, Curr Opin Cell Biol., 25(2):241-246 (2013).
Duan, Y. et al., Differentiation and Enrichment of Hepatocyte-Like Cells from Human Embryonic Stem Cells in Vitro and In Vivo, Stem Cells, 25(12):3058-3068 (2007).
Hay, D.C. et al., Efficient Differentiation of Hepatocytes From Human Embryonic Stem Cells Exhibiting Markers Recapitulating Liver Development in Vivo, Stem Cells, 26(4):894-902 (2008).
Hay, D.C. et al., Highly efficient differentiation of hESCs to functional hepatic endoderm requires ActivinA and Wnt3a signaling, PNAS, 105(34):12301-12306 (2008).
International Search Report for PCT/SG2015/050325, 5 pages (Nov. 13, 2015).
Kobayashi, N. et al., Prevention of Acute Liver Failure in Rats with Reversibly Immortalized Human Hepatocytes, Science, 287(5456):1258-1264 (2000).
Kondo, Y. et al., Histone Deacetylase Inhibitor Valproic Acid Promotes the Differentiation of Human Induced Pluripotent Stem Cells Into Hepatocyte Like Cells, PLoS One, 9(8):1-11(2014).
Kostrubsky, V.E. et al., The Use of Human Hepatocyte Cultures to Study the Inductoin of Cytochrome P-450, Drug Metabolism and Disposition, 27(8):887-894 (1999).
Koyama, T. et al., Efficient Proliferation and Maturation of Fetal Liver Cells in Three-Dimensional Culture by Stimulation of Oncostatin M, Epidermal Growth Factor, and Dimethyl Sulfoxide, Tissue Engineering: Part A, 15(5):1099-1107 (2009).
Lavon, N. et al., Differentiation and isolation of hepatic-like cells from human embryonic stem cells, Differentiation, 72:230-238 (2004).
Li, A.P. et al., Preclinical evaluation of drug-drug interaction potential: present status of the application of primary human hepatocytes in the evaluation of cytochrome P450 induction, Chemico-Biological Interactions, 107:5-16 (1997).
McLean, A.B. et al., Activin A Efficiently Specifies Definitive Endoderm from Human Embryonic Stem Cells Only When Phosphatidylinositol 3-Kinase Signaling Is Suppressed, Stem Cells, 25(1):29-38 (2007).
Mitaka, T. et al., The current status of primary hepatocyte culture, Int. J. Exp. Path., 79:393-409 (1998).
Nyberg, S.L. et al., Primary Hepatocytes Outperform Hep G2 Cells as the Sorce of Biotransformation Functions in a Bioartificial Liver, Annals of Surgery, 220(1):59-67 (1994).
Patel, S. et al., Glycogen Synthase Kinase-3 in Insulin and Wnt Signalling: a Double-edged Sword?, Biochem Soc Trans, 32(Pt. 5):803-808 (2004).
Pfeifer, A.M.A. et al., Simian virus 40 large tumor antigen-immortalized normal human liver epithelial cells express hepatocyte characteristics and metabolize chemical carcinogens, Prov. Natl. Acad. Sci. USA, 90:5123-5127 (1993).
Rambhatla, L. et al., Generation of Hepatocyte-Like Cells From Human Embryonic Stem Cells, Cell Transplantation, 12:1-11 (2003).
Robb, L. and Tam, P.P.L., Gastrula organiser and embryonic patterning in the mouse, Seminars in Cell & Developmental Biology, 15:543-554 (2004).
Roelandt, P. et al., Human Embryonic and Rat Adult Stem Cells with Primitive Endoderm-Like Phenotype Can Be Fated to Definitive Endoderm, and Finally Hepatocyte-Like Cells, PLoS One, 5(8):e12101 (2010).
Rogler, L.E. et al., Selective Biopotential Differentiation of Mouse Embryonic Hepatoblasts In Vitro, American Journal of Pathology, 150(2):591-602 (1997).
Runge, D. et al., Recent Advances in Human Hepatocyte Culture Systems, 274:1-3 (2000).
Sakai, Y. et al., Enhanced In Vitro Maturation of Fetal Mouse Liver Cells with Oncostatin M, Nicotinamide, and Dimethyl Sulfoxide, Cell Transplantation, 11:435-441 (2002).
Schwartz, R.E. et al., Defined Conditions for Development of Functional Hepatic Cells from Human Embryonic Stem Cells, Stem Cells and Development, 14:643-655 (2005).
Shan, J. et al., Indentification of small molecules for human hepatocyte expansion and iPS differentiation, Nat Chem Biol., 9(8):514-520 (2013).

(56) References Cited

OTHER PUBLICATIONS

Siller, R. et al., Small-Molecule-Driven Hepatocyte Differentiation of Human Pluripotent Stem Cells, Stem Cell Reports, 4(5):939-952 (2015).
Silva, J.M. et al., Refinement of an in vitro cell model for cytochrome P450 induction, Drug Metabolism and Disposition, 26(5):490-496 (1998).
Strom, S.C. et al., Hepatocyte transplantation as a bridge to orthotopic liver transplantation in terminal liver failure, 63(4):559-569 (1997).
Strom, S.C. et al., Hepatocyte Transplantatoin for the Treatment of Human Disease, Seminars in Liver Disease, 19(1):39-48 (1999).
Tahamtani, Y. et al., Treatment of Human Embryonic Stem Cells with Different Combinations of Priming and Inducing Factors Toward Definitive Endoderm, Stem Cells Dev., 22(9):1419-1432 (2013).
Tasnim, F. et al., Cost-effective Differentiation of Hepatocyte-like Cells From Human Pluripotent Stem Cells Using Small Molecules, Biomaterials, 70:115-125 (2015).
Thomson, J.A. et al., Embryonic Stem Cell Lines Derived from Human Blastocytes, Science, 282(5391):1145-1147 (1998).
Touboul, T. et al., Generation of Functional Hepatocytes from Human Embryonic Stem Cells Under Chemically Defined Conditions that Recapitulate Liver Development, Hepatology, 51(5):1754-1765 (2010).
Written Opinion for PCT/2015/050325, 8 pages (Nov. 13, 2015).
Brolén, G. et al., Hepatocyte-like cells derived from human embryonic stem cells specifically via definitive endoderm and a progenitor stage, Journal of Biotechnology, 145: 284-294 (2010).

\* cited by examiner

DIFFERENTIATION OF HEPATOCYTE-LIKE CELLS FROM STEM CELLS

CROSS-REFERENCE TO RELATED APPLICATIONS

This patent application is a National Stage Entry of International Patent Application No. PCT/SG2015/050325, filed on Sep. 17, 2015 which claims the benefit of priority of Singapore provisional application No. 10201405916Y, filed 19 Sep. 2014, the contents of each of which are hereby incorporated by reference in their entirety for all purposes herein.

FIELD OF THE INVENTION

The present invention relates to developmental biology. In particular, the present invention also relates to compositions for differentiating stem cells into more hepatocytes-like cells. The present invention also relates to methods for differentiating stem cells into more hepatocytes-like cells using the compositions thereof.

BACKGROUND OF THE INVENTION

Human hepatocytes are valuable tools for hepatotoxicity screening, a crucial step for drug discovery and development. In addition, hepatocyte transplantation has proved to be a promising alternative to orthotropic liver transplantation. The current cellular system of choice for drug screening and cell therapy is primary human hepatocyte (PH). However, the utility of primary human hepatocyte in either clinical or pharmaceutical applications is limited by their availability, donor variability, limited proliferation and decline in function over extended culture periods. Therefore, substantial effort has been put into the derivation of alternative expandable sources of functional hepatocytes which can counteract the disadvantages associated with primary human hepatocyte.

Human embryonic stem cells (hESCs) provide an attractive alternative cell source to primary human hepatocyte, due to their unlimited proliferative and pluripotent differentiative capacity. Accordingly, there is a need to provide for a method for obtaining and maintaining hepatocyte-like cells that represent adult hepatocytes phenotype.

SUMMARY OF THE INVENTION

In one aspect, there is provided a method of differentiating definitive endoderm in order to obtain hepatocyte-like cells. In one example, the method comprising the steps of a) subjecting definitive endoderm to at least one epigenetic modulator to obtain hepatoblasts, b) subjecting the hepatoblasts to at least one stem cell differentiation pathway inhibitor to obtain hepatocyte-like cells; wherein steps a) and b) do not comprise the use of a growth factor.

In another aspect, there is provided a hepatocyte-like cell obtained by or obtainable by the method as described herein.

In yet another aspect, there is provided a use of the hepatocyte-like cell as described herein in an application selected from a group consisting of drug toxicity screening, drug cytotoxicity assessment cell therapy, tissue engineering and tissue regeneration.

BRIEF DESCRIPTION OF THE DRAWINGS

The invention will be better understood with reference to the detailed description when considered in conjunction with the non-limiting examples and the accompanying drawings, in which:

In FIG. 2, "NaBu" refers to sodium butyrate; "LY" refers to LY294002; "Act" refers to Activin A; "GAPDH" refers to Glyceraldehyde 3-phosphate dehydrogenase. Thus, FIG. 2 shows that treatment with the small molecules in combination with Activin A results in inducing definitive endoderm (DE) differentiation.

FIG. 3 shows that hepatoblasts are generated during the differentiation process and that small-molecule-based induction (method as described herein) was comparable to the growth factor based induction (method as known in the art).

FIG. 4 shows relative expression of hepatic markers of hepatocytes derived from hESCs using small molecules. Results are plotted relative to control enzyme GAPDH (Glyceraldehyde 3-phosphate dehydrogenase). Following generation of hepatoblasts (FIG. 3), cells were treated with either SB431542/DMSO for 8 days, (labeled as small-molecule based maturation) or with HGF and Follistatin for 6 days (labeled as growth factor based maturation). The total time period for differentiation for both small molecule and growth factor based approaches was 20 days (FIG. 1). Bars show average±s.d (n=3). Thus, FIG. 4 shows the hepatocytes obtained from either method as illustrated in FIG. 1 produces similar hepatic markers profile.

FIG. 5 shows hepatocytes obtained from either method as illustrated in FIG. 1 can produce albumin, urea and CYP1A2 and CYp3A4.

FIG. 6 shows the results of an example of an application of cells obtained from the method of differentiating as described herein in drug testing. The cell viability of small molecules (SM-Hep), growth factors (GF-Hep), and primary human hepatocytes (PH) were assessed by MTS cell-viability assay after 24 hour exposure to different concentrations of test compounds. Cell viability is expressed as a percentage of cells treated with solvent only. Bars show average±s.d (n=3). Thus, FIG. 6 shows that the susceptibility of small molecules-derived hepatocytes (SM-Hep) was similar to that of the growth factors-derived (GF-Hep) hepatocytes.

FIG. 8 shows the combination of Activin A, LY294002 and BIO can induce definitive endoderm formation.

FIG. 9 shows none of the combinations as tested are effective in replacing Activin A signaling.

FIG. 10 shows small molecules can initiate hepatic differentiation from definitive endoderm without the use of any growth factors.

FIG. 11 shows the differentiation of hepatocytes from hepatic progenitors using methods as described herein.

FIG. 12 shows the hepatocytes resulted from the method as described herein are functionally comparable to hepatocytes resulted from methods known in the art.

FIG. 13 shows the hepatocytes as derived from the method as described herein may be used for drug testing.

BRIEF DESCRIPTION OF THE TABLE

Figure 1:
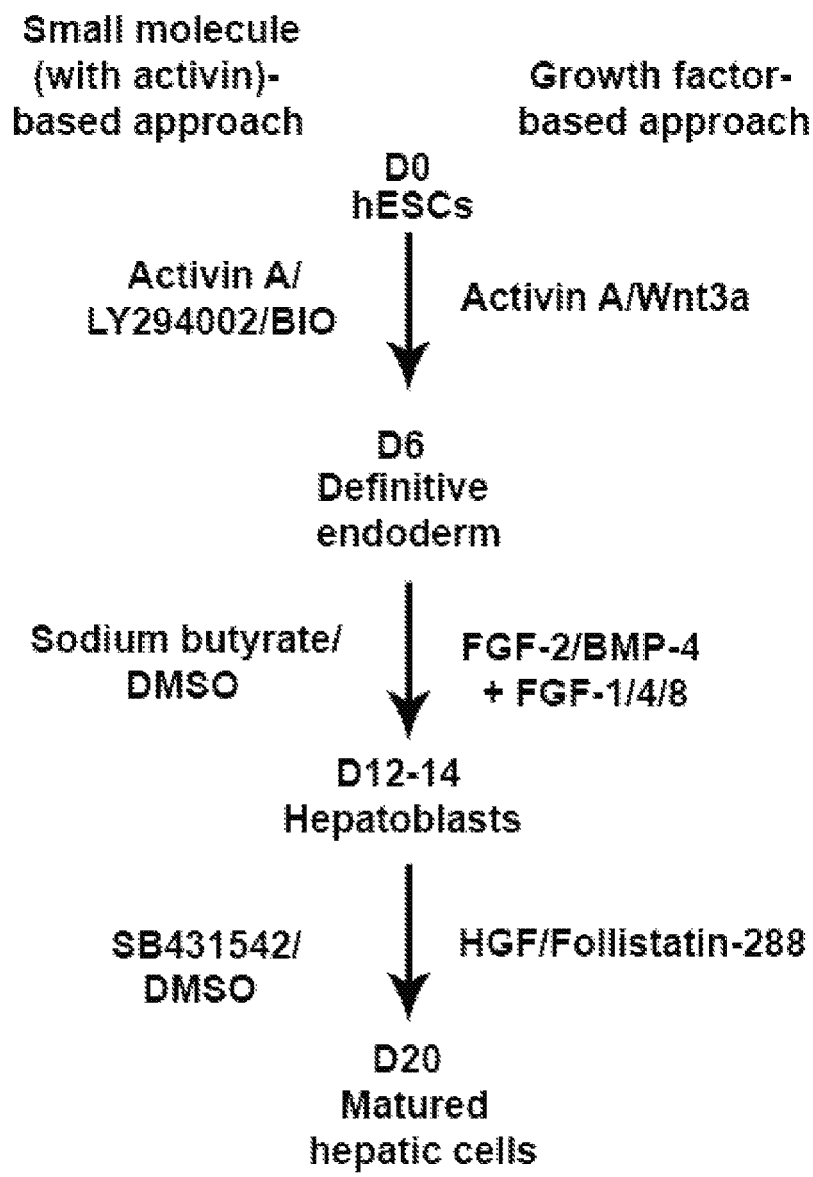
FIG. 1 shows a schematic representation that illustrates the three-step protocol used to differentiate human embryonic stem cells (hESCs) to hepatocytes. The left hand column shows an example of the protocol as described herein. The right hand column illustrates the growth-factor based protocol as known in the art. The growth factor based protocol as known in the art was used as a control for analyzing the effects of substituting growth factors with small molecules.

The invention will be better understood with reference to the detailed description when considered in conjunction with the non-limiting examples and the accompanying Table, in which:

Table 1 shows the IC50 values for hepatotoxicity screening using hepatocytes differentiated using growth factors (GF) or small molecules (SM).

Table 2 shows the updated $IC_{50}$ values for hepatotoxicity screening using hepatocytes differentiated using growth factors (GF) or small molecules (SM).

DETAILED DESCRIPTION OF THE PRESENT INVENTION

Functional human hepatocytes have a wide variety of applications, particularly in cell therapy and hepatotoxicity screening. Due to the limited availability and challenges associated with the use of primary human hepatocytes, great efforts have been put into generating hepatocytes from stem cells. Accordingly, there is a need to provide an alternative method of differentiating stem cells into hepatocytes.

A step-wise differentiation protocol for differentiating human embryonic stem cells into functional hepatocytes using predominantly small molecules (and Activin A as the only growth factor) was developed. As used herein, the term "small molecules" refers to molecules of low molecular weight, e.g. 900 Daltons and less. This definition may also refer to organic compounds that may help regulate a biological process, with a size on the order of $10^{-9}$ m, i.e. within the nanometer range.

It is found that differentiation of hepatocytes from stem cells usually follows at least three steps (i) differentiation of stem cells to a definitive endoderm form, (ii) differentiation of definitive endoderm to hepatic progenitors/hepatoblasts, and (iii) differentiation of functional hepatocytes or hepatocytes-like cells from the hepatic progenitors/hepatoblasts. The present inventors investigated the use of small molecules in the context of how it modulated a particular signalling pathway. For example, a variety of small molecules based on their effects on signalling pathways was tested alone or in combination of varying steps for their ability to generate definitive endoderm from pluripotent stem cells (i.e. step i). Once the right combination was identified, treatment with small molecules for Step ii and thereafter Step iii) was analysed similarly. Thus, the inventors of the present disclosure have found an alternative method of differentiating stem cells into functional hepatocytes/hepatocytes-like cells that addresses the three steps differentiation mentioned above.

Thus, in one example, there is provided a method of differentiating definitive endoderm in order to obtain hepatocyte-like cells. In one example, the method comprising step a) subjecting definitive endoderm to at least one epigenetic modulator to obtain hepatoblasts. In one example, the method may further comprises step b) subjecting the hepatoblasts to at least one stem cell differentiation pathway inhibitor to obtain hepatocyte-like cells. In one example, in the method as described herein, steps a) and b) do not comprise the use of a growth factor. That is, in one example, in the method as described herein, steps a) and b) are growth factor-free. In one example, the method as described herein may comprise step a) subjecting definitive endoderm to a growth factor free medium comprising at least one epigenetic modulator to obtain hepatoblasts. In one example, the method may further comprises step b) subjecting the hepatoblasts to a growth factor free medium comprising at least one stem cell differentiation pathway inhibitor to obtain hepatocyte-like cells. In one example, step a) refers to differentiation step ii) above, which relates to the differentiation of definitive endoderm into hepatoblasts/hepatic progenitors; and step b) refers to differentiation step iii) above, which relates to the differentiation of hepatoblasts/hepatic progenitors into hepatocytes/hepatocyte-like cells.

In one example, there is provided a method of differentiating stem cells in order to obtain hepatocyte-like cells. In one example, the method of differentiating stem cell as described herein may comprise the step of subjecting stem cells to at least one compound, which regulates stem cell differentiation by inhibiting kinase activity, to obtain definitive endoderm cells. In one example, the method may further comprise the step of subjecting definitive endoderm cells to at least one epigenetic modulator to obtain hepatoblasts, and wherein this step does not comprise the use of a growth factor. In one example, the method may further comprise the step of subjecting the hepatoblasts to at least one stem cell differentiation pathway inhibitor to obtain hepatocyte-like cells, and wherein this step does not comprise the use of a growth factor. In one example, any of the steps as provided may be followed chronologically or may include additional steps that are known in the art. In one example, there is provided a method of differentiating stem cells in order to obtain hepatocyte-like cells, the method may comprise the steps of: subjecting stem cells to at least one compound, which regulates stem cell differentiation by inhibiting kinase activity, to obtain definitive endoderm cells; subjecting definitive endoderm cells to at least one epigenetic modulator to obtain hepatoblasts, and wherein this step does not comprise the use of a growth factor; and subjecting the hepatoblasts to at least one stem cell differentiation pathway inhibitor to obtain hepatocyte-like cells, and wherein this step does not comprise the use of a growth factor.

As used herein the term "differentiating", "differentiation", or other grammatical permutations thereof, refers to the process by which an unspecialized ("uncommitted") or less specialized cell acquires the features of a specialized cell such as, for example, a nerve cell, a liver cell (such as hepatocytes) or a muscle cell. A differentiated or differentiation-induced cell is one that has taken on a more specialized ("committed") position within the lineage of a cell. Once a cell has differentiated or committed, the cell would have proceeded in the differentiation pathway to a point where, under normal circumstances, it will continue to differentiate into a specific cell type or subset of cell types, and cannot, under normal circumstances, differentiate into a different cell type or revert to a less differentiated cell type. A lineage-specific marker refers to a characteristic specifically associated with the phenotype of cells of a lineage of interest and can be used to assess the differentiation of an uncommitted cell to the lineage of interest.

As used herein, the term "stem cells" refers to undifferentiated cells defined by their ability at the single cell level to both self-renew and differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation and to contribute substantially to most, if not all, tissues following injection into blastocysts.

Stem cells are classified by their developmental potential as: (1) totipotent, meaning able to give rise to all embryonic and extra embryonic cell types; (2) pluripotent, meaning able to give rise to all embryonic cell types; (3) multipotent, meaning able to give rise to a subset of cell lineages but all within a particular tissue, organ, or physiological system (for example, hematopoietic stem cells (HSC) can produce progeny that include HSC (self-renewal), blood cell restricted oligopotent progenitors, and all cell types and elements (e.g., platelets) that are normal components of the blood); (4) oligopotent, meaning able to give rise to a more restricted subset of cell lineages than multipotent stem cells; and (5) unipotent, meaning able to give rise to a single cell lineage (e.g. spermatogenic stem cells). In one example, as used herein, the term "stem cells" does not include human embryonic stem cells that can give rise to all embryonic and extraembryonic cell types, which can subsequently develop into a human. In one example, the stem cells may be pluripotent stem cells or multipotent stem cells.

Pluripotent stem cells may express one or more of the stage-specific embryonic antigens (SSEA) 3 and 4, and markers detectable using antibodies designated Tra-1-60 and Tra-1-81. Differentiation of pluripotent stem cells in vitro results in the loss of SSEA-4, Tra-1-60, and Tra-1-81 expression (if present) and increased expression of SSEA-I. Undifferentiated pluripotent stem cells typically have alkaline phosphatase activity, which can be detected by methods known in the art, for example by fixing the cells with 4% paraformaldehyde, and then developing with Vector Red as a substrate, as described by the manufacturer (Vector Laboratories, Burlingame Calif.) Undifferentiated pluripotent stem cells also typically express Oct-4 and TERT, as detected by RT-PCR.

Another phenotype of propagated pluripotent stem cells is a potential to differentiate into cells of all three germinal layers: endoderm, mesoderm, and ectoderm tissues. Thus, in one example, pluripotency of pluripotent stem cells may be confirmed by injecting cells into severe combined immunodeficient (SCID) mice, fixing the teratomas that form using 4% paraformaldehyde, and then examining them histologically for evidence of cell types from the three germ layers. Alternatively, pluripotency may be determined by the creation of embryoid bodies and assessing the embryoid bodies for the presence of markers associated with the three germinal layers.

In one example, propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

The types of pluripotent stem cells that may be used include established lines of pluripotent cells derived from tissue formed after gestation, including pre-embryonic tissue (such as, for example, a blastocyst), embryonic tissue, or fetal tissue taken any time during gestation, typically but not necessarily before approximately 10-12 weeks gestation. In one example, established lines of human embryonic stem cells or human embryonic germ cells, may include, but are not limited to, the human embryonic stem cell lines H1, H7, and H9 (WICELL™). Also contemplated is use of the compositions of the present disclosure during the initial establishment or stabilization of such cells, in which case the source cells would be primary pluripotent cells taken directly from the source tissues. Also suitable are cells taken from a pluripotent stem cell population already cultured in the absence of feeder cells. Also suitable are mutant human embryonic stem cell lines, such as, for example, BGOIv (BresaGen, Athens, Ga.). Thus, in one example, the pluripotent stem cells may be an induced pluripotent stem cells or of naturally pluripotent stem cells. In one example, the stem cells may be derived from cells such as, but are not limited to, of liver-derived cells, pancreas-derived cells, umbilical cord-derived cells, umbilical cord blood derived cells, brain-derived cells, spleen-derived cells, bone marrow derived cells, heart-derived cells, lung derived cells, adipose derived cells, cells derived from IPS technology, cells derived from embryonic stem cells, genetically engineered cells, pluripotent cells, multipotent cells, neural cells, astrocytes, hepatocytes, fibroblasts, mesenchymal cells, pericytes, cardiomyocytes, cardiomyocyte progenitor cells, hematopoietic cells, endothelial cells, endothelial progenitor cells, smooth muscle cells, keratinocytes, progenitor cells, cell mixtures and combinations thereof. In one example, the stem cells may be H9 cells. In one example, the stem cells may be grown using methods known in the art. In one example, the stem cells may be grown in feeder-cell-free culture. In one example, the stem cells may be culture as adherent cells or suspended cells (suspension cells).

In one example, the stem cells as used in the present disclosure may be mammalian cells.

As used herein, the term "definitive endoderm" refers to cells which bear the characteristics of cells arising from the epiblast during gastrulation and which form the gastrointestinal tract and its derivatives. The term "definitive endoderm" may also refer cells expressing markers characteristics of definitive endoderm lineage such as, but are not limited to FoxA2, HNF3 beta, GATA4, SOX17, Cerberus, OTX2, goosecoid, C-Kit, CD99, GSC, Cerl, Nodal, FGF8, Barchyury, Mix-like homeobox protein (MIXL1), FGF4 CD48, eomesodermin (EOMES), DKK4, GATA6, FGF17, and CXCR4. As known in the art, it may not be practical to check all markers to confirm on whether a cell may be identified as a definitive endoderm. Thus, in one example, the definitive endoderm cells may at least express at least two of the markers, such as, but is not limited to, FoxA2, HNF3 beta, GATA4, SOX17, Cerberus, OTX2, goosecoid, C-Kit, CD99, GSC, Cerl, Nodal, FGF8, Barchyury, Mix-like homeobox protein (MIXL1), FGF4 CD48, eomesodermin (EOMES), DKK4, GATA6, FGF17, and CXCR4. In one example, a cell may be determined to be a definitive endoderm cell if it expresses at least FoxA2 and SOX17. In one example, the cells may be determined to be a definitive endoderm if the cell has also less pluripotency markers (as compared to stem cells) when the cells are being driven towards the definitive endoderm.

As used herein, the term "hepatoblast" refers to the progenitor cells of hepatocyte-like or hepatocyte. In one example, hepatoblast refers to cells that express markers at least one of markers associated with hepatoblasts, such as, but are not limited to, hepatocytes nuclear factor 4 alpha (HNF4α), hepatocytes nuclear factor 3 beta (HNF3-13), cytokeratin 18 (CK18), Albumin, biliary marker CK19, and AFP (alpha-feto protein). In one example, the hepatoblast cells may be further characterized by their capability to be driven further to hepatocytes and still have proliferative capacity. In one example, hepatoblasts may be differentiated from the definitive endoderm state through loss of some (but not all) definitive endoderm markers such as SOX17. In one example, the hepatoblasts may have higher expression of AFP and lower expression of hepatic markers (Albumin, cytochrome P450 enzymes) compared to hepatocyte-like cells. In one example, hepatoblasts may have a combination of some of the hepatoblast markers such as, but are not limited to, HNF4α, AFP, and CK18/CK19, to be identified as a hepatoblast.

As used herein, the term "hepatocyte-like" refers to cells that express at least two hepatocyte markers, such as, but are not limited to, expression of albumin, ccFP, hepatocytes nuclear factor 4 alpha (HNF4α), hepatocytes nuclear factor 3 beta (HNF3-β), cytokeratin 18 (CK18), glutamine synthetase (GS), more disorganized smooth muscle actin (SMA), and Von Willebrand Factor (VWF). In one example, markers may also include hepatocyte-inducible genes such as, but is not limited to, androstane receptor (CAR), pregnane X receptor (PXR), peroxisome proliferators-activated receptor Y coactivatoMα (PGC-1), Phosphoenol pyruvate carboxykinase (PEPCK) and peroxisome proliferators-activated receptor-γ (PPAR-Y), (key gluconeogenic enzymes), CYP3A4 (a cytochrome P450 (CYP) Phase I monooxygenase system enzyme important for endo- and xenobiotic metabolism). In one example, these inducible genes have either elevated expression in the differentiated hepatocyte-like cells or can be induced in upon treatment with PB, RIF, 8-Br-cAMP or forskolin. Additional relevant hepatocyte markers that may be expressed by the hepatocyte-like cells may include, but are not limited to, albumin production; product of 7-pentoxyresorufin-O-dealkylation (PROD), which is catalyzed specifically by CYP2B1/2; the enzyme required for hepatic bilirubin elimination, UDP-glucuronosyltransferase (UGT1A1); Human hydroxysteroid sulfotransferase (SULT2A1) which catalyzes the sulfonation and detoxication of endogenous and xenobiotic substrates; transthyretin (TTR)1 tryptophan-2,3-dioxygenase (TDO); alfa-1-antitrypsin (alfa-1-AT), Liver-Specific Organic Anion Transporter (LST-1, also called OATP2); and carbamoyl phosphate synthase 1 (CPSase-1). In one example, hepatocyte-like cellular markers may include, but are not limited to, morphological characteristics such as being mostly mononuclear and heterogeneous with high nucleus to cytoplasmic ratio, more polygonal to cuboidal shape, displaying lipid droplet inclusions, ability to form cannicular type structures, and ability to develop sinusoids. In yet another example, hepatocyte-like cells may be characterized as having characteristics such as, but are not limited to, glycogen production, synthesis of serum proteins, plasma proteins, clotting factors, detoxification functions, urea production, gluconeogenesis and lipid metabolism. Thus, in one example, the hepatocyte-like cells express more mature hepatocyte functions, such as functioning metabolic pathways. Thus, in one example, the hepatocyte-like cells may be characterized by selecting at least two methods such as, but are not limited to, morphological analysis, gene expression level analysis of hepatic markers, transcription factor analysis, functional assays, cytochrome (CYP) analysis, drug testing applications and the like. In one example, the functional assays may include, but are not limited to, glycogen uptake assay, LDL storage assay, Indocyanine green (iCG) uptake assay and clearance assay. In one example, the hepatocyte-like cells may be characterized by morphological analysis and cytochrome (CYP) analysis. In one example, the target of the cytochrome (CYP) analysis may include proteins belonging to the superfamily cytochrome P450. As would be appreciated by the person skilled in the art, there are various methods of determining whether a cell can be identified as a hepatocyte. For example, the state of the art uses a combination of some of the assays described herein to identify a cell as hepatocyte. In one example, gene expression, albumin/urea production or glycogen uptake, as well as some of the CYP activities are the minimal assays required. In one example, more than one assay may be required in determining whether a cell is a hepatocyte. In one example, a combination of assays as described herein may be used to confirm that the cell is a hepatocyte.

In one example, the hepatocyte-like cells may be primary human hepatocytes.

Figure 4:
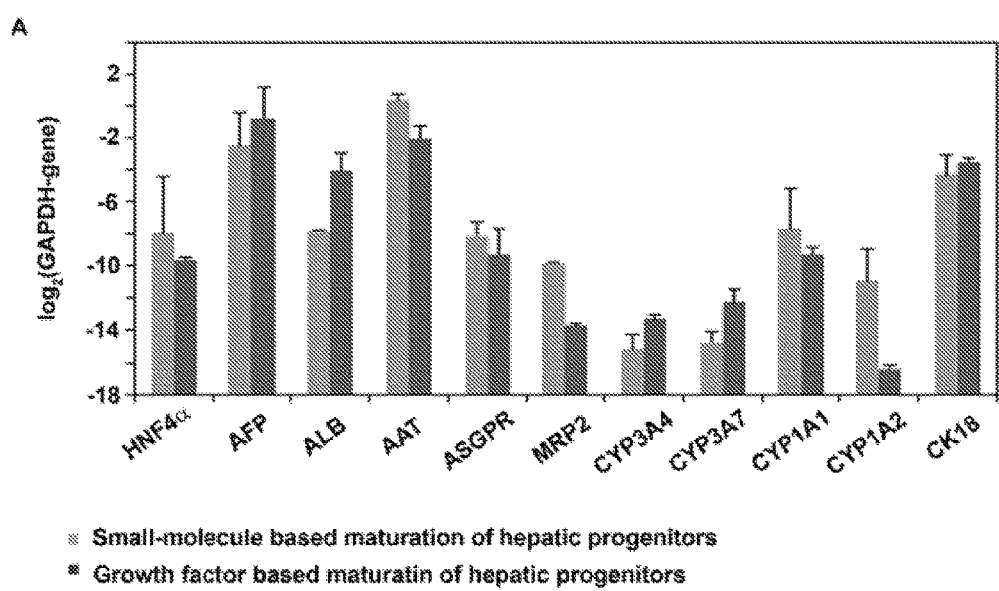
FIG. 4 shows a bar graph depicting the results of qPCR analysis showing expression of hepatic marker genes at the end of the 20 days differentiation period (of culture with either methods as described in FIG. 1).
Figure 5:
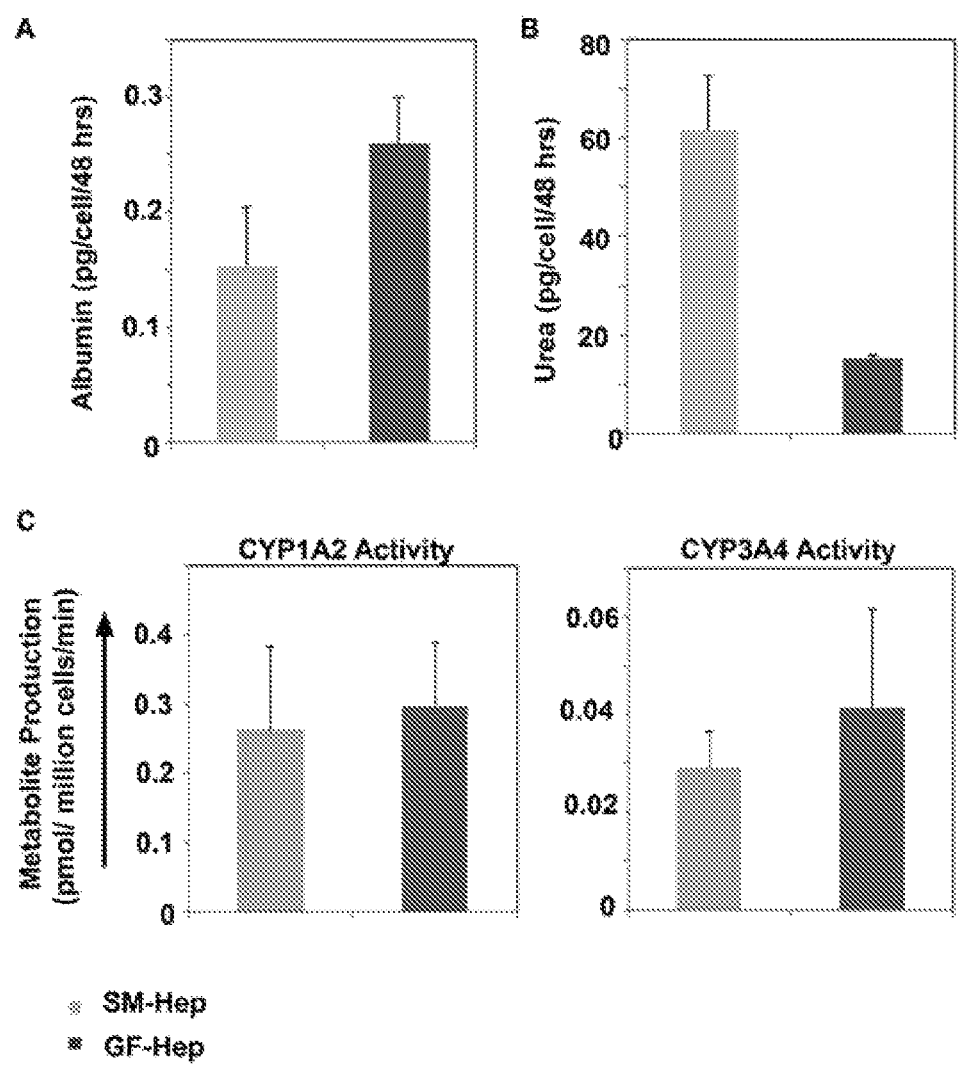
FIG. 5 shows functional performance of hepatocytes derived from human embryonic stem cells (hESCs) using small molecules (SM-Hep) and growth factors (GF-Hep). In particular, (A) shows bar graph of Albumin production; (B) shows bar graph of Urea production; and (C) shows bar graph of CYP1A2 and CYp3A4 specific metabolite production of hepatocytes obtained from hESCs using either small molecules (SM-Hep) or growth factors (GF-Hep). Briefly, cells were differentiated using either small molecules or growth factors for 20 days before supernatant was collected at day 20 for measuring albumin and urea production. Differentiated cells were treated with CYP1A2 and CYp3A4 specific substrates for quantifying metabolite production. The amount of albumin, urea and metabolite produced were normalized to cell numbers. Bars show average±s.d (n=3). Thus.

As illustrated in the Example section and FIGS. 4 and 5, the functionalities of the hepatocytes/hepatocytes-like cells were confirmed using gene expression of hepatic markers, production of albumin and urea, and basal and induced levels of major cytochrome P450 enzymes, such as CYP1A2 and CYP3A4. In one example, the hepatocyte-like cells may be confirmed using at least one, at least two or all of the methods known in the art, such as gene expression of hepatic markers, production of albumin and urea, and basal and induced levels of major cytochrome P450 enzymes, such as CYP1A2 and CYP3A4.

As used herein, the term "epigenetic modulator" refers to a molecule or agent capable of reactivating regulator genes that have been repressed in a cell, such as a stem cell. As used herein, the "epigenetic modulator" causes meiotically and mitotically heritable changes in gene expression that are not due to shifts in the bases within DNA. Examples are DNA methylation genes and their inhibitors, histone modifications agents (such as histone deactelysases or histone deactelysases inhibitors (HDACIs), chromatin remodeling, microRNA as well as other noncoding regulatory RNA. In one example, epigenetic modulators may be referred as chromatin remodeling agents that can regulate stem cell differentiation. In one example, the epigenetic modulator may be include, but is not limited to, DNA methylation agents and their inhibitors, histone modifications agents, chromatin remodelling, microRNAs and non-coding regulatory RNA. In one example, the histone modification agents may include, but is not limited to histone deacetylases and histone deacetylase inhibitors (HDACi).

In one example, the "epigenetic modulator" may be present in a concentration of about 100-200 nM, or about 200-400 nM, or about 400-600 nM, or about 600-800 nM, or about 800-1000 nM, or about 250-500 nM, or about 750-1000 nM. In one example, the "epigenetic modulator" may be present in a concentration of about 100-500 nM, or about 150-300 nM, or about 200-300 nM, or about 210-290 nM, or about 220-280 nM, or about 230-270 nM, or about 240-260 nM, or about 200 nM, or about 210 nM, or about 220 nM, or about 230 nM, or about 240 nM, or about 250 nM, or about 260 nM, or about 270 nM, or about 280 nM, or about 290 nM, or about 300 nM. In one example, the epigenetic modulator may be provided in a concentration of about 0.1-2%, or about 0.1-1.5%, or about 0.1-1%, or about 0.25-0.75%, or about 0.3-0.6% or about 0.5% of total volume.

As illustrated in the Example section, the method as described herein may subject the definitive endoderm to two epigenetic modulators. Thus, in one example, step a) of the method as described herein may comprise two epigenetic modulators. Without wishing to be bound by theory, the inventors of the present disclosure found the combination of two epigenetic modulators surprisingly resulted in high levels of hepatic marker expression and reduced cell death.

In one example, the method as described herein may subject the hepatoblast to two stem cell differentiation pathway inhibitors. Thus, in one example, step b) of the method as described herein may comprise two stem cell differentiation pathway inhibitors.

Alternatively, in one example, the method as described herein may subject the hepatoblast to a stem cell differentiation pathway inhibitor and an epigenetic modulator. Thus, in one example, step b) of the method as described herein may comprise a stem cell differentiation pathway inhibitor and an epigenetic modulator. In one example, when step b) of the method comprises a stem cell differentiation pathway inhibitor and an epigenetic modulator, the epigenetic modulator in step a) of the method as described herein may be lower than in step b) of the method as described herein.

Thus, in one example where the epigenetic modulator is histone modification agent, the histone modification agent as provided in step a) of the method as described herein may be lower than in step b) of the method as described herein. In one example, where the epigenetic modulator is histone deacetylase inhibitor, the histone deacetylase inhibitor as provided in step a) of the method as described herein may be lower than in step b) of the method as described herein.

In one example, the histone deacetylase inhibitor may include, but is not limited to sodium butyrate, dimethyl sulfoxide (DMSO) and the like. In one example, the epigenetic modulator may be histone deacetylase inhibitor, such as sodium butyrate and/or dimethyl sulfoxide (DMSO).

In one example, the sodium butyrate may be provided in a concentration of about 100-500 nM, or about 150-300 nM, or about 200-300 nM, or about 210-290 nM, or about 220-280 nM, or about 230-270 nM, or about 240-260 nM, or about 200 nM, or about 210 nM, or about 220 nM, or about 230 nM, or about 240 nM, or about 250 nM, or about 260 nM, or about 270 nM, or about 280 nM, or about 290 nM, or about 300 nM.

In one example, the concentration of the histone deacetylase inhibitor may be provided in percentage concentration of the total volume of solution. Thus, in one example, the concentration of the histone deacetylase inhibitor in either step a) or b) may be about 0.1-2%, or about 0.1-0.5%, or about 0.5-0.1%, or about 0.5-1%, or about 1-1.5% or about 1.5-2%.

In one example, the histone deacetylase inhibitor may be dimethyl sulfoxide (DMSO) and the concentration in step a) and/or step b) may be about 0.1-2%, or about 0.1-0.5%, or about 0.5-0.1%, or about 0.5-1%, or about 1-1.5% or about 1.5-2%. In one example, the histone deacetylase inhibitor may be dimethyl sulfoxide (DMSO) and the concentration in step a) and/or step b) may be about 0.1-2%, or about 0.1-1.5%, or about 0.25-1.25%, or about 0.3-1.1%, or about 0.5-1%. In one example, the histone deacetylase inhibitor may be dimethyl sulfoxide (DMSO) and the concentration in step a) and/or step b) may be about 0.1%, or about 0.2%, or about 0.3%, or about 0.4%, or about 0.5%, or about 0.6%, or about 0.7%, or about 0.8%, or about 0.9%, or about 1%, or about 1.1%, or about 1.2%, or about 1.3%, or about 1.4%, or about 1.5%.

In one example, the histone deacetylase inhibitor may be dimethyl sulfoxide (DMSO) and the concentration in step a) may be about 0.1%, or about 0.2%, or about 0.3%, or about 0.4%, or about 0.5%, or about 0.6%.

In one example, the histone deacetylase inhibitor may be dimethyl sulfoxide (DMSO) and the concentration in step b) may be about 0.6%, or about 0.7%, or about 0.8%, or about 0.9%, or about 1%, or about 1.1%, or about 1.2%, or about 1.3%, or about 1.4%, or about 1.5%.

As used herein, the term "inhibit" or "block" means a reduction in the level of activity of a particular signaling pathway of a cell upon treatment with a compound (i.e. an inhibitor) compared to the activity of said signaling pathway of a cell that is left untreated with such compound or treated with a control. Thus, as used herein, the term "stem cell differentiation pathway inhibitor" refers to a molecule (i.e. an inhibitor), which can reduce the differentiation activity or stops the differentiation pathway of a stem cell compared to the activity of the stem cell that is left untreated with such compound or treated with a control. In one example, the stem cell differentiation pathway inhibitors may affect at least one, at least two, at least three or all of the differentiation pathway known in the art such as, but is not limited to, Notch pathway, bone morphogenic proteins (BMP) pathway, fibroblast growth factor (FGF) pathway, transforming growth factor beta (TGFβ) pathway and the like. In one example, the stem cell differentiation pathway inhibitor may include, but is not limited to, adrenomedullin inhibitors, angiopoietin inhibitors, autocrine motility factor inhibitors, bone morphogenetic protein inhibitors, brain-derived neurotrophic factor inhibitors, epidermal growth factor inhibitors, erythropoietin inhibitors, fibroblast growth factor inhibitors, glial cell line-derived neurotrophic factor inhibitors, granulocyte colony-stimulating factor inhibitors, granulocyte macrophage colony-stimulating factor inhibitors, growth differentiation factor-9 inhibitors, healing factor inhibitor, hepatocyte growth factor inhibitors, hepatoma-derived growth factor inhibitors, insulin-like growth factor inhibitors, keratinocyte growth factor inhibitors, migration-stimulating factor inhibitors, myostatin inhibitors, nerve growth factor inhibitors, neurotrophin inhibitors, platelet-derived growth factor inhibitors, thrombopoietin inhibitors, transforming growth factor alpha inhibitors, transforming growth factor beta inhibitors, tumour necrosis factor-alpha inhibitors, vascular endothelial growth factor inhibitors, Wnt signalling pathway inhibitors, placental growth factor inhibitors, foetal bovine somatotrophin inhibitors, interleukin inhibitors and combinations thereof. In one example, the stem cell differentiation pathway inhibitor may include, but is not limited to, epidermal growth factor inhibitors, hepatocyte growth factor inhibitors, hepatoma-derived growth factor inhibitors, insulin-like growth factor inhibitors, thrombopoietin inhibitors, transforming growth factor alpha inhibitors, transforming growth factor beta inhibitors, Wnt signalling pathway inhibitors, and the like In one example, the stem cell differentiation pathway inhibitor may be provided in the method in a concentration that would be apparent by the person skilled in the art. In one example, the stem cell differentiation pathway inhibitor may be present in a concentration of about 0.1-5 µM, about 5-10 µM, or about 10-25 µM, or about 25-50 µM, or about 8-16 µM or about 15-30 µM. In one example, the stem cell differentiation pathway inhibitor may be present in a concentration of about 0.1-5 µM, or about 0.2-4 µM, or about 0.3-3 µM, or about 0.4-2 µM, or about 0.5-1.75 µM, or about 0.6-1.5 µM, or about 0.7-1.25 µM, or about 0.8-1.1 µM, or about 0.9-1 µM, or about 0.1 µM, or about 0.2 µM, or about 0.3 µM, or about 0.4 µM, or about 0.5 µM, or about 0.6 µM, or about 0.7 µM, or about 0.8 µM, or about 0.9 µM, or about 1 µM, or about 1.1 µM, or about 1.2 µM, or about 1.3 µM, or about 1.4 µM, or about 1.5 µM, or about 1.6 µM, or about 1.7 µM, or about 1.8 µM, or about 1.9 µM, or about 2.0 µM. In one example, the stem cell differentiation pathway inhibitor may be a transforming growth factor beta inhibitor (TGF-β inhibitor).

As used herein, the term "growth factor inhibitor" refers to compounds that inhibit, stop, or reduce (as compared to control or untreated) pathways involved in stem cell differentiation. This may include Notch pathway, BMP, FGF pathway and TGFβ pathway. Similar TGFβ is known to promote cholangiocytes differentiation and therefore TGFβ inhibition has the potential to be used as a method of promoting hepatocyte differentiation occurs at the expense of the impairment of cholangiocyte differentiation. In one example, the transforming growth factor beta inhibitor may include, but is not limited to, dimethyl sulfoxide (DMSO), 4-(4-(benzo[d][1,3]dioxol-5-yl)-5-(pyridin-2-yl)-1H-imidazol-2-yl)benzamide (SB431542), 3-(6-Methyl-2-pyridinyl)-N-phenyl-4-(4-quinolinyl)-1H-pyrazole-1-carbothioamide (A83-01), 4-[4-(2,3-Dihydro-1,4-benzodioxin-6-yl)-5-(2-pyridinyl)-1H-imidazol-2-yl]benzamide (D4476), 4-[4-[3-(2-Pyridinyl)-1H-pyrazol-4-yl]-2-pyridinyl]-N-(tetrahydro-2H-pyran-4-yl)-benzamide (GW788388), 4-[3-(2-Pyridinyl)-1H-pyrazol-4-yl]-quinoline (LY364947), 2-(3-(6-Methylpyridine-2-yl)-1H-pyrazol-4-yl)-1,5-naphthyridine (RepSox), 2-[4-(1,3-Benzodioxol-5-yl)-2-(1, 1-dimethylethyl)-1H-imidazol-5-yl]-6-methyl-pyridine (SB505124), 6-[2-(1,1-Dimethylethyl)-5-(6-methyl-2-pyridinyl)-1H-imidazol-4-yl]quinoxaline (SB525334), 2-(5-Chloro-2-fluorophenyl)-4-[(4-pyridyl)amino]pteridine (SD208), deadenylating nuclease (DAN), and a combination thereof. As illustrated in the Example section, SB431542 was used in this study. One further inhibitor is deadenylating nuclease (DAN). Thus, in one example, the stem cell differentiation pathway inhibitor may be SB431542 and/or deadenylating nuclease (DAN).

As used herein, the term "growth factor" refers to a polynucleotide molecule, polypeptide molecule, or other related chemical agent that is capable of effectuating differentiation of cells. For example, "growth factor" may refer to compounds that stimulate pathways involved in stem cell differentiation. Examples of growth factors may include, but are not limited to, cytokines, hormones, and compounds that bind cell-surface receptors on their target, which activates growth or differentiation related pathways. Examples of growth factors may include, but are not limited to, a epidermal growth factor (EGF), transforming growth factor-alpha (TGF-alpha), transforming growth factor-beta (TGF-beta), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), and/or platelet derived growth factor (PDGF). In one example, the growth factors may include, but are not limited to, a epidermal growth factor (EGF), transforming growth factor-alpha (TGF-alpha), transforming growth factor-beta (TGF-beta), bone morphogenetic protein (BMP), fibroblast growth factor (FGF), insulin-like growth factor (IGF), and the like. In one example, the growth factor may be activin. In one example, the activin may be Activin A, Activin B or a dimer of Activin A and B (Activin AB).

As used herein, the phrase "do not comprise" refers to the absence of exogenously added agent or molecule. Thus, in the present disclosure, the phrase "do not comprise the use of a growth factor" refers to the absence of the addition of exogenous growth factor in the method as described herein (such as steps a) and b)).

In one example, step a) of the method as described herein may include subjecting the definitive endoderm to epigenetic modulators such as, but are not limited to, sodium butyrate and dimethyl sulfoxide (DMSO). As illustrated in the Example section, the addition of these epigenetic modulators was shown to successfully generate hepatic progenitors/hepatoblasts from the definitive endoderm. In one example, step b) of the method as described herein may include subjecting the hepatoblasts/hepatic progenitors obtained from step b) with at least one cell differentiation pathway inhibitor such as SB431542 (a transforming growth factor β/TGF-beta inhibitor) and DMSO. As illustrated in the Example section, the addition of the stem cell differentiation pathway inhibitor was shown to successfully generate functional hepatocytes/hepatocytes-like cells.

Figure 7:
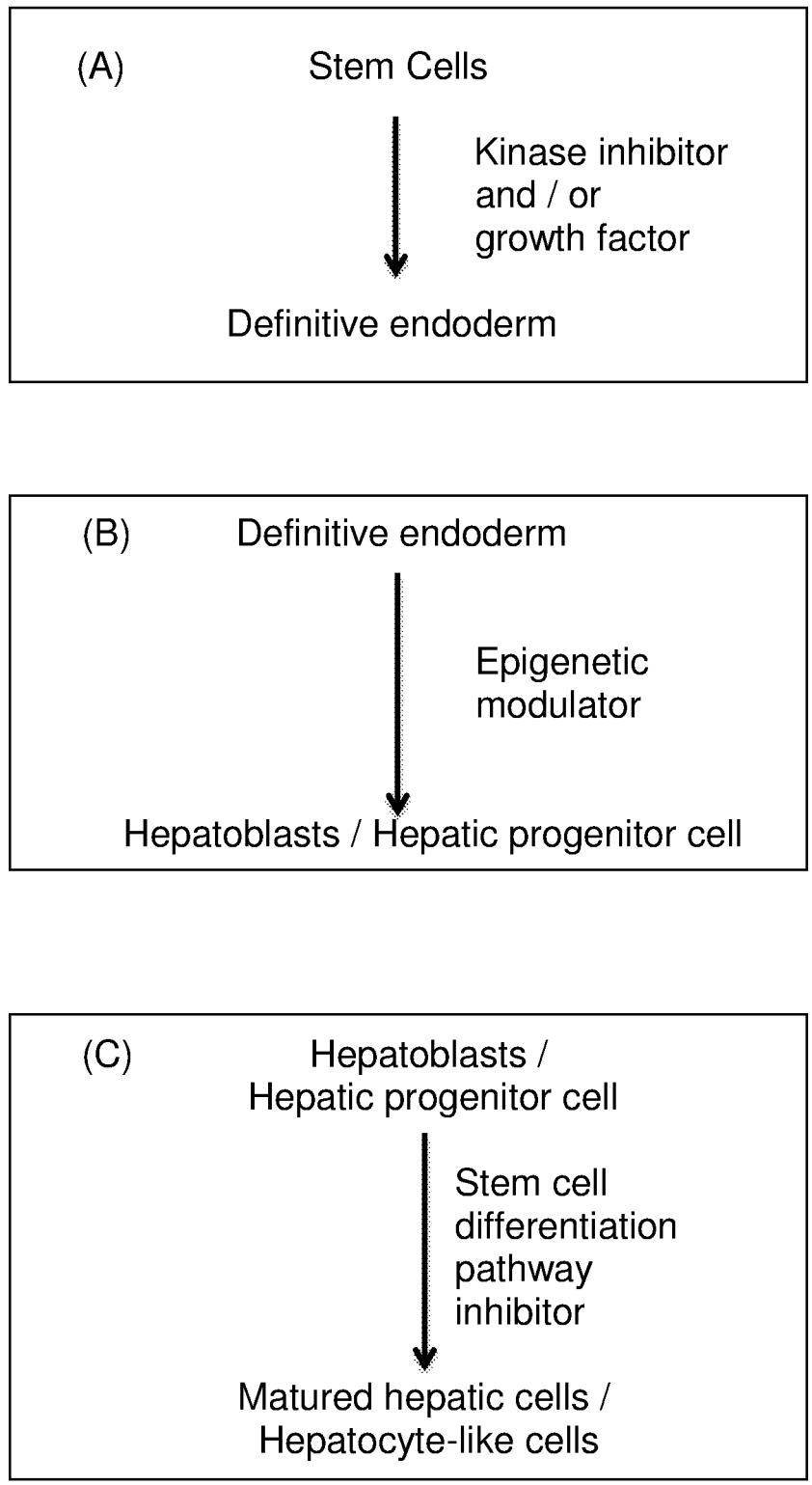
FIG. 7 shows generalized schematic representations of the various steps in the method as described herein. In particular, (A) shows differentiation of stem cells into definitive endoderm; (B) shows differentiation of definitive endoderm into hepatoblasts/hepatic progenitor cells; and (C) shows differentiation of hepatic progenitor cells/hepatoblasts into matured hepatocytes or hepatocyte-like cells.

As illustrated in the Example section, FIG. 1 and FIG. 7, to provide for a definitive endoderm, the human embryonic stem cell was subjected to at least one compound that can regulate stem cell differentiation. Thus, in one example, before step a) in the method as described herein, the definitive endoderm may be obtained by subjecting the stem cells to at least one compound which regulates stem cell differentiation by inhibiting kinase activity. In one example, the step "prior to" or "before" step a) refers to differentiation step i) discussed above, which relates to the differentiation of stem cells into definitive endoderm.

As used herein, the term "kinase inhibitor" refers to molecules, which inhibits, reduced or stops kinase-signalling pathway in a cell as compared to cells that were not subjected to the same compound (untreated) or a control. Kinase inhibitors are classified as 1) tyrosine kinase inhibitors (both receptor tyrosine kinase inhibitors such and non-receptor tyrosine kinase inhibitors 2) serine/threonine kinase inhibitors and 3) kinase inhibitors which act on all 3 residues-serine, threonine and tyrosine. Here, kinase inhibitors as compounds, which regulate stem cell differentiation by inhibiting kinase activity. Examples of such kinase inhibitors include, but are not limited to: phosphoinositide-3-kinase (PI3K) inhibitor LY294002, wortmannin, PX-866 (Oncothyreon), SF1126; Dual pI3K-mTor inhibitors: PI-103, GDC-0941, NVP-BEZ235 (Novartis), GDC-0980 (Genentech), XL-765 (Exelixis), GSK2126458 (GlaxoSmithKline), PKI-587/PF-05212384 (Wyeth), PF-04691502 (Pfizer) Y-27632 (Rho-associated kinase inhibitor); Glycogen synthase 3 kinase inhibitor 6-bromoindirubin-3'-oxime (BIO); and the like.

In one example, the step before step a) of the method as described herein (step where definitive endoderm may be obtained from stem cells) may further comprise a growth factor for obtaining definitive endoderm (from stem cells). In one example, the growth factor may be activin, such as Activin A, Activin AB or Activin B.

In one example, in the step before step a) of the method as described herein (step where definitive endoderm may be obtained from stem cells), at least two, or at least three or at least four, or more compounds, which regulate stem cell differentiation by inhibiting kinase activity, may be used to obtain definitive endoderm. In one example, at least two compounds, which can regulate stem cell differentiation by inhibiting kinase activity, may be used to obtain definitive endoderm. In one example, one of the at least two compound that can obtain definitive endoderm may be a compound that regulates stem cell differentiation by inhibiting kinase activity. In one example, the compound that can be used to obtain definitive endoderm may be a phosphoinositide-3-kinase inhibitor. In one example, the compound may be a glycogen synthase 3 inhibitor. Thus, in one example, in the step before step a) of the method as described herein, at least two compounds, which regulate stem cell differentiation by inhibiting kinase activity, may be used to obtain definitive endoderm, wherein one compound which regulates stem cell differentiation by inhibiting kinase activity may be a phosphoinositide-3-kinase inhibitor. In one example, wherein in the step before step a) of the method as described herein, the at least two compounds, which regulate stem cell differentiation by inhibiting kinase activity, may be used to obtain definitive endoderm, wherein one compound may be a glycogen synthase 3 inhibitor.

In one example, the compound, which regulates stem cell differentiation by inhibiting kinase activity, may be present in a concentration of about 0.1-20 µM, or about 0.5-10 µM, or about 1-20 µM, or about 1.5-15 µM or about 1.75-12 µM or about 2-10 µM. In one example, when the compound, which regulates stem cell differentiation by inhibiting kinase activity may be present in a concentration of about 0.1-20 µM, about 0.5-15 µM, about 0.75-10 µM, or about 0.1 µM, or about 0.2 µM, or about 0.3 µM, or about 0.4 µM, or about 0.5 µM, or about 0.6 µM, or about 0.7 µM, or about 0.8 µM, or about 0.9 µM, or about 1.0 µM, or about 1.1 µM, or about 1.2 µM, or about 1.3 µM, or about 1.4 µM, or about 1.5 µM, or about 1.6 µM, or about 1.7 µM, or about 1.8 µM, or about 1.9 µM, or about 2.0 µM, or about 2.1 µM, or about 2.2 µM, or about 2.3 µM.

In one example, when the compound, which regulates stem cell differentiation by inhibiting kinase activity may be present in a concentration of about 0.1-20 µM, about 5-15 µM, about 7.5-12.5 µM, or about 1 µM, or about 2 µM, or about 3 µM, or about 4 µM, or about 5 µM, or about 6 µM, or about 7 µM, or about 8 µM, or about 9 µM, or about 10 µM, or about 11 µM, or about 12 µM, or about 13 µM, or about 14 µM, or about 15 µM, or about 16 µM, or about 17 µM, or about 18 µM, or about 19 µM, or about 20 µM.

In one example, when the compound, which regulates stem cell differentiation by inhibiting kinase activity, is 6-bromoindirubin-3'-oxime (BIO), the compound may be present in a concentration of about 0.1-20 µM, about 0.5-15 µM, about 0.75-10 µM, or about 0.1 µM, or about 0.2 µM, or about 0.3 µM, or about 0.4 µM, or about 0.5 µM, or about 0.6 µM, or about 0.7 µM, or about 0.8 µM, or about 0.9 µM, or about 1.0 µM, or about 1.1 µM, or about 1.2 µM, or about 1.3 µM, or about 1.4 µM, or about 1.5 µM, or about 1.6 µM, or about 1.7 µM, or about 1.8 µM, or about 1.9 µM, or about 2.0 µM, or about 2.1 µM, or about 2.2 µM, or about 2.3 µM.

In one example, when the compound, which regulates stem cell differentiation by inhibiting kinase activity, is LY2947002, the compound may be present in a concentration of about 0.1-20 µM, about 5-15 µM, about 7.5-12.5 µM, or about 1 µM, or about 2 µM, or about 3 µM, or about 4 µM, or about 5 µM, or about 6 µM, or about 7 µM, or about 8 µM, or about 9 µM, or about 10 µM, or about 11 µM, or about 12 µM, or about 13 µM, or about 14 µM, or about 15 µM, or about 16 µM, or about 17 µM, or about 18 µM, or about 19 µM, or about 20 µM.

In one example, the compound, which regulates stem cell differentiation by inhibiting kinase activity, may act on the transforming growth factor beta (TGF-β) family/the SMAD signalling pathway/Activin and Wnt signalling pathways/phosphoinositide-3-kinase (PI3K)-AKT signalling pathway. In one example, the compound, which regulates stem cell differentiation by inhibiting kinase activity, may include, but is not limited to, 2-Morpholin-4-yl-8-phenylchromen-4-one (LY294002), (1alpha,11alpha)-11-(Acetyloxy)-1-(methoxymethyl)-2-oxaandrosta-5,8-dieno(6,5,4-bc)furan-3,7,17-trione (Wortmannin), (1E,4S,4aR,5R,6aS,9aR)-5-(acetyloxy)-1-[(di-2-propen-1-ylamino)methylene]-4,4a,5,6,6a,8,9,9a-octahydro-11-hydroxy-4-(methoxymethyl)-4a,6a-dimethyl-cyclopenta[5,6]naphtho[1,2-c]pyran-2,7,10 (1H)-trione (PX-866), (8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate (SF1126), 3-[4-(4-morpholinyl)pyrido[3',2':4,5]furo[3,2-d]pyrimidin-2-yl]-phenol (PI-103), 2-(1H-indazol-4-yl)-6-(4-methanesulfonyl-piperazin-1-ylmethyl)-4-morpholin-4-yl-thieno[3,2-d]pyrimidine (GDC-0941), 4-[2,3-dihydro-3-methyl-2-oxo-8-(3-quinolinyl)-1H-imidazo[4,5-c]quinolin-1-yl]-α,α-dimethyl-benzeneacetonitrile (NVP-BEZ235), (S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (GDC-0980), 2-amino-8-ethyl-4-methyl-6-(1H-pyrazol-3-yl)pyrido[2,3-d]pyrimidin-7(8H)-one (SAR245409, XL-765), 2,4-Difluoro-N-{2-(methyloxy)-5-[4-(4-pyridazinyl)-6-quinolinyl]-3-pyridinyl}benzenesulfonamide (GSK2126458), 1-(4-(4-(dimethylamino)piperidine-1-carbonyl)phenyl)-3-(4-(4, 6-dimorpholino-1,3,5-triazin-2-yl)phenyl)urea (PKI-587/ PF-05212384), 2-amino-8-[trans-4-(2-hydroxyethoxy) cyclohexyl]-6-(6-methoxy-3-pyridinyl)-4-methyl-pyrido[2, 3-d]pyrimidin-7(8H)-one (PF-04691502), glycogen synthase-3-kinase inhibitors, phosphoinositide-3-kinase inhibitors and 6-bromoindirubin-3'-oxime (BIO).

In one example, the glycogen synthase 3 kinase inhibitors may include, but is not limited to, Valproic Acid (Sodium Salt), (5S,6R,7R,9R)-6-methoxy-5-methyl-7-methylamino-6,7,8,9,15,16-hexahydro-5H,14H-5,9-epoxy-4b,9a,15-triazadibenzo[b,h]cyclonona[1,2,3,4-jkl]cyclopenta[e]-as-indacen-14-one (Staurosporine), (9R,10S,12S)-2,3,9,10,11, 12-Hexahydro-10-hydroxy-9-methyl-1-oxo-9,12-epoxy-1H-diindol-o[1,2,3-fg:3',2',1'-kl]pyrrolo[3,4-i][1,6] benzodiazocine-10-carboxylic acid, hexyl ester (KT 5720), (2Z,3E)-6'-Bromo-3-(hydroxyimino)-[2,3'-biindolinylidene]-2'-one (GSK-3 Inhibitor IX), Bisindolylmaleimide IX (Ro 21-8220), 3-(2,4-Dichlorophenyl)-4-(1-methyl-1H-indol-3-yl)-1H-pyrrole-2,5-dione (SB-216763), 2,3,4,5-Tetrahydro-7-hydroxy-1H-benzofuro[2,3-c]azepin-1-one (CID 755673), 9-Bromo-7,12-dihydroindolo[3,2-d][1]benzazepin-6(5H)-one (Kenpaullone), lithium chloride, 3-(6-(3-aminophenyl)-7H-pyrrolo[2,3-d]pyrimidin-4-yloxy)phenol (GSK-3β Inhibitor XII), 6-(2-(4-(2,4-Dichlorophenyl)-5-(4-methyl-1H-imidazol-2-yl)-pyrimidin-2-ylamino)ethylamino)-nicotinonitrile (GSK-3 Inhibitor XVI), 4Z)-4-(2-Amino-5-oxo-3,5-dihydro-4H-imidazol-4-ylidene)-2-bromo-4,5,6,7-tetrahydropyrrolo[2,3-c]azepin-8(1H)-one (10Z-Hymenialdisine), 2-(2-oxo-1H-indol-3-ylidene)-1H-indol-3-one (Indirubin), N6-[2-[[4-(2,4-dichlorophenyl)-5-(1H-imidazol-1-yl)-2-pyrimidinyl]amino]ethyl]-3-nitro-2, 6-Pyridinediamine (CHIR-98014), 2-Chloro-1-(4,5-dibromo-thiophen-2-yl)-ethanone (GSK-3β Inhibitor VI), Keramamine A (Manzamine A), 3-[1,3-Dihydro-3-(hydroxyimino)-2H-indol-2-ylidene]-1,3-dihydro-2H-indol-2-one (Indirubin-3'-monoxime), 6-Bromoindirubin-3'-acetoxime (GSK-3 Inhibitor X), GSK-3 Inhibitor XV

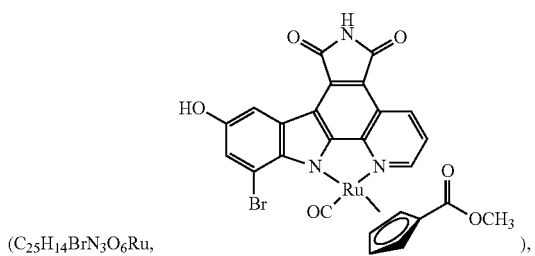

(C25H14BrN3O6Ru, ),

3-[(3-Chloro-4-hydroxyphenyl)amino]-4-(2-nitrophenyl)-1H-pyrrole-2,5-dione (SB-415286), 9-Bromo-7,12-dihydropyrido[3',2':2,3]azepino[4,5-b]indol-6(5H)-one (1-Azakenpaullone), 3-[6-(3-amino-phenyl)-7H-pyrrolo[2,3-D] pyrimidin-4-yloxy]-phenol (TWS 119 ditrifluoroacetate), 5-Iodoindirubin-3'-monoxime, 2,4'-Dibromoacetophenone (GSK-3β Inhibitor VII), 3-Amino-1H-pyrazolo[3,4-b]quinoxaline (Cdk1/5 Inhibitor), 2-Debromooroidin (Hymenidin), Bisindolylmaleimide X hydrochloride, 5-ethyl-7,8-dimethoxypyrrolo[3,4-c]isoquinoline-1,3-dione (3F8), Imidazo[1',5':1,6]pyrrolo[3',4':4,5]pyrido[2,3-b]indole-1,3 (2H,8H)-dione (isogranulatimide), (2R)-2-({9-(1-methylethyl)-6-[(4-pyridin-2-ylbenzyl)amino]-9H-purin-2-yl}amino)butan-1-ol (CR8, R-Isomer), 2-chloro-5-(2-phenyl-5-(pyridin-4-yl)-1H-imidazol-4-yl)phenol (Raf Kinase Inhibitor IV), Indirubin-3'-monoxime-5-sulphonic acid, 2-Thio(3-iodobenzyl)-5-(1-pyridyl)-[1,3,4]-oxadiazole (GSK-3 Inhibitor II), N-(4-Methoxybenzyl)-N'-(5-nitro-1,3-thiazol-2-yl)urea (GSK-3β Inhibitor VIII), 7-n-butyl-6-(4'-hydroxyphenyl)-5H-pyrrolo(2,3b)pyrazine (Aloisine A), 3-(1-(3-Hydroxypropyl)-1H-pyrrolo[2,3-b]pyridin-3-yl]-4-pyrazin-2-yl-pyrrole-2,5-dione (GSK-3β Inhibitor XI), 1-Methyl-BIO (GSK-3 Inhibitor IX, Control MeBio, CAS 710323-61-8), 3-(6-Oxo-9-nitro-5,6,7,12-tetrahydroindolo [3,2-d][1]benzazepin-2-yl)propionitrile (Alsterpaullone), 1,3,4-Oxadiazole, 2-methyl-5-[3-[4-(methylsulfinyl)phenyl]-5-benzofuranyl]-(TCS 2002), 3-[5-[4-(2-Hydroxy-2-methyl-1-oxopropyl)-1-piperazinyl]-2-(trifluoromethyl) phenyl]-4-(1H-indol-3-yl)-1H-pyrrole-2,5-dione (TCS 21311), 6-oxo-7,12-dihydro-5H-indolo[3,2-d][1]benzazepine-9-carbonitrile (9-Cyanopaullone), Indirubin-5-sulfonic acid sodium salt, 4-Benzyl-2-methyl-1,2,4-thiadiazolidine-3,5-dione (GSK-3β Inhibitor I) and 1-(7-Methoxyquinolin-4-yl)-3-[6-(trifluoromethyl)pyridin-2-yl] urea (A 1070722).

In one example, there is provided a method of differentiating stem cells in order to obtain hepatocyte-like cells. In one example, the method may include any combinations of the examples of steps as described below. For example, in one example, the method may include all three steps as illustrated in FIG. 7. In another example, the method may only include a method of differentiating definitive endoderm to hepatocyte-like cells. In one example, the method may only include a method of differentiating hepatoblast to hepatocyte-like cells. In one example, the method may only include a method of differentiating definitive endoderm to hepatoblast.

In one example, the method of differentiating stem cell as described herein may comprise the step of subjecting stem cells to at least one compound, which regulates stem cell differentiation by inhibiting kinase activity, to obtain definitive endoderm cells.

In one example, the method of differentiating stem cell to definitive endoderm may comprise the step of subjecting the stem cells to a kinase inhibitor and a growth factor.

In one example, the method of differentiating stem cell to definitive endoderm may comprise the step of subjecting the stem cells to a kinase inhibitor and an activin.

In one example, the method of differentiating stem cell to definitive endoderm may comprise the step of subjecting the stem cells to a phosphoinositide-3-kinase inhibitor and a growth factor.

In one example, the method of differentiating stem cell to definitive endoderm may comprise the step of subjecting the stem cells to a glycogen synthase 3 inhibitor and a growth factor.

In one example, the method of differentiating stem cell to definitive endoderm may comprise the step of subjecting the stem cells to a glycogen synthase 3 inhibitor, a phosphoinositide-3-kinase inhibitor, and a growth factor.

In one example, the method of differentiating stem cell to definitive endoderm may comprise the step of subjecting the stem cells to a glycogen synthase 3 inhibitor, a phosphoinositide-3-kinase inhibitor, and an activin.

In one example, the method of differentiating stem cell to definitive endoderm may comprise the step of subjecting the stem cells to a glycogen synthase 3 inhibitor, a phosphoinositide-3-kinase inhibitor, and a growth factor.

In one example, the method of differentiating stem cell to definitive endoderm may comprise the step of subjecting the stem cells to compounds that acts on the transforming growth factor beta (TGF-beta) family/the SMAD signaling pathway/Activin and Wnt signaling pathways/phosphoinositide-3-kinase-AKT signaling pathway.

In one example, the method of differentiating stem cell to definitive endoderm may comprise the step of subjecting the stem cells to a bromo-indirubin-3'-oxime (BIO), a phosphoinositide-3-kinase inhibitor, and a growth factor. In one example, the method of differentiating stem cell to definitive endoderm may comprise the step of subjecting the stem cells to a glycogen synthase 3 inhibitor, LY294002, and a growth factor.

In one example, the method of differentiating stem cell to definitive endoderm may comprise the step of subjecting the stem cells to a bromo-indirubin-3'-oxime (BIO), a LY294002, and a growth factor.

In one example, the method of differentiating stem cell to definitive endoderm may comprise the step of subjecting the stem cells to a bromo-indirubin-3'-oxime (BIO), a LY294002, and an activin.

In one example, the method may comprise the step of differentiating definitive endoderm to hepatoblasts, wherein the method comprises the step of subjecting the definitive endoderm to at least one epigenetic modulator, and wherein this step does not comprise the use of a growth factor.

In one example, the method may comprise the step of differentiating definitive endoderm to hepatoblasts, the method comprises the step of subjecting the definitive endoderm to DNA methylation agents, and wherein this step does not comprise the use of a growth factor.

In one example, the method may comprise the step of differentiating definitive endoderm to hepatoblasts, wherein the method comprises the step of subjecting the definitive endoderm to histone modification agents, and wherein this step does not comprise the use of a growth factor.

In one example, the method may comprise the step of differentiating definitive endoderm to hepatoblasts, wherein the method comprises the step of subjecting the definitive endoderm to an agent capable of chromatin remodeling, wherein this step does not comprise the use of a growth factor.

In one example, the method may comprise the step of differentiating definitive endoderm to hepatoblasts, wherein the method comprises the step of subjecting the definitive endoderm to histone deacetylases and/or histone deacetylase inhibitors (HDACi), wherein this step does not comprise the use of a growth factor.

In one example, the method may comprise the step of differentiating definitive endoderm to hepatoblasts, wherein the method comprises the step of subjecting the definitive endoderm to dimethyl sulfoxide and/or sodium butyrate, wherein this step does not comprise the use of a growth factor.

In one example, the method may comprise the step of differentiating a hepatoblast to a hepatocyte-like cell, wherein the method comprises the step of subjecting a hepatoblast to at least one stem cell differentiation pathway inhibitor to obtain hepatocyte-like cells, and wherein this step does not comprise the use of a growth factor.

In one example, the method may comprise the step of differentiating a hepatoblast to a hepatocyte-like cell, wherein the method comprises the step of subjecting a hepatoblast to transforming growth factor beta inhibitor to obtain hepatocyte-like cells, and wherein this step does not comprise the use of a growth factor.

In one example, the method may comprise the step of differentiating a hepatoblast to a hepatocyte-like cell, wherein the method comprises the step of subjecting a hepatoblast to dimethyl sulfoxide (DMSO) and/or SB431542 to obtain hepatocyte-like cells, and wherein this step does not comprise the use of a growth factor.

In one example, any of the compounds as used herein may be natural (isolated from naturally occurring sources), synthetic or semi-synthetic. In one example, the epigenetic modulator and/or the stem cell differentiation pathway inhibitor may be natural (isolated from naturally occurring sources, without manipulation by the hand of man, except for isolation purposes), synthetic or semi-synthetic.

Figure 6:
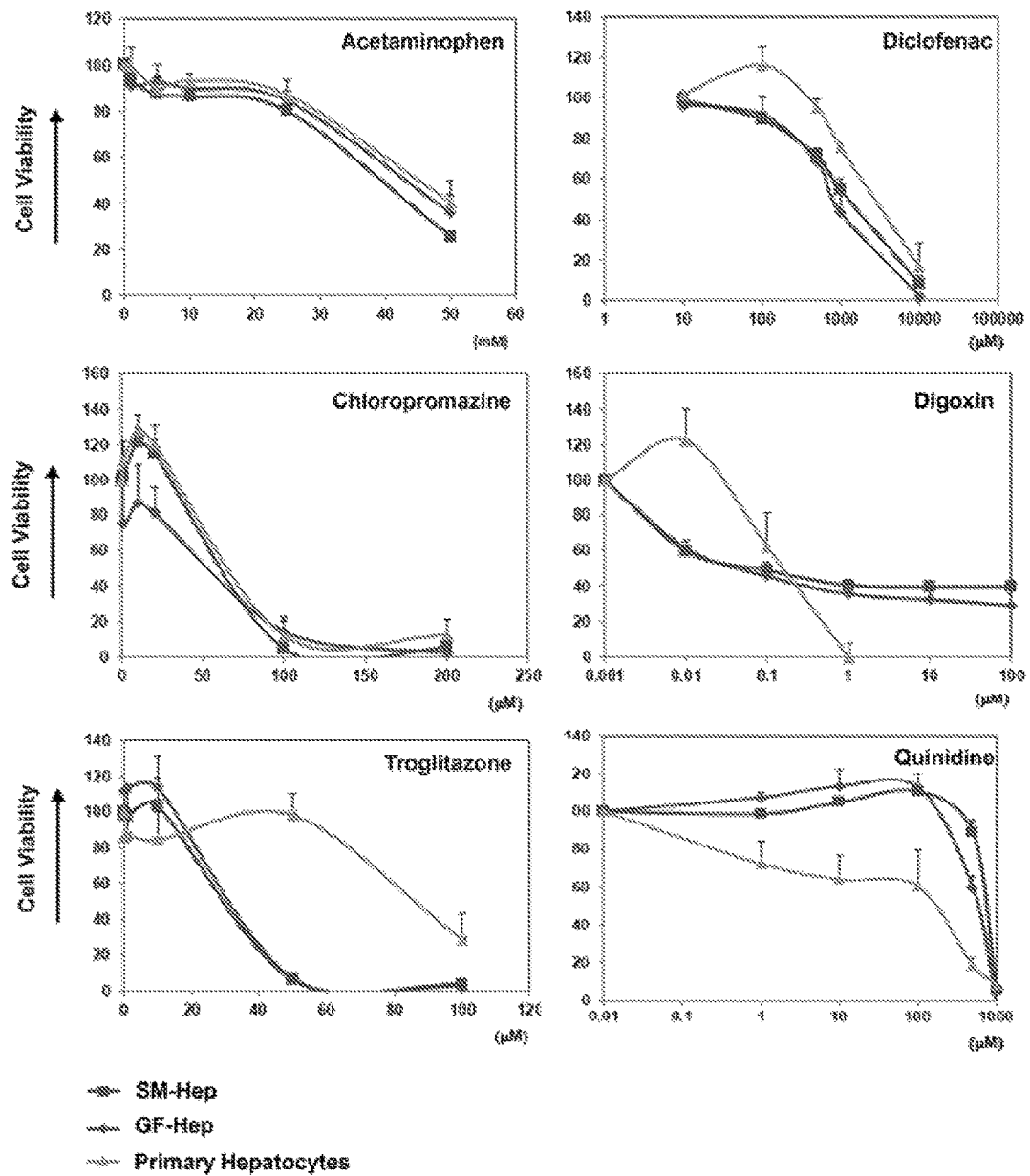
FIG. 6 shows a graph depicting percentage cell viability upon treatment with drug.

As illustrated in FIG. 6, the hepatocytes generated using the method as described herein may serve as a cost-efficient tool for large-scale applications, such as hepatotoxicity screening. Thus, in one example, there is provided a hepatocyte-like cell obtained by or obtainable by the method of as described herein. In a further example, there is provided the use of the hepatocyte-like cell as obtained from the method as described herein in an application such as, but is not limited to, drug toxicity screening, drug cytotoxicity assessment cell therapy, tissue engineering, tissue regeneration, and the like. In one example, there is provided a method of screening drug. In one example, the method of screening drug may comprise subjecting the hepatocyte-like cell according to claim 19 to a test sample. In one example, the method of screening drug may further comprise measuring the viability of the hepatocyte-like cell and/or measuring the functional phenotype of the hepatocyte-like cell. In one example, the drug screening may be for an application such as, but is not limited to, drug toxicity screening, drug cytotoxicity assessment cell therapy, tissue engineering, tissue regeneration, and the like.

In one example, there is provided a kit comprising a composition for use in differentiating stem cell into definitive endoderm (i.e. step i, or step prior to or before step a of method as described herein), and/or a composition for use in differentiating definitive endoderm into hepatoblasts/hepatic progenitor cells (i.e. step ii, or step a of method as described herein), and/or a composition for use in differentiating hepatoblasts/hepatic progenitor cells into hepatocyte-like/hepatocytes (i.e. step iii, or step b of method as described herein). The compositions for specific differentiation steps are as those used in the methods as described herein.

In one example, there is provided a drug screening kit comprising the hepatocyte-like cells as obtained by the method as described herein. In one example, the drug screening kit may further comprise reagents for drug screening including, but are not limited to, culture media, reagents for detecting albumin, hepatocyte functions, and the like.

In one example, the definitive endoderm may be obtained by subjecting human embryonic stem cells to at least one, or at least two, or at least all of Activin A, LY294002 (a phosphoinositide3 kinase inhibitor) and bromo-indirubin-3'-oxime (BIO, a glycogen synthase kinase 3 inhibitor).

In one example, the method as described herein may be performed by the method as summarized in FIG. 1 (left column). In one example, the compounds as used in the Example section (as summarized in FIG. 1 (left column)) may include, the components as listed in the following table and may be provided in the concentration as provided in the following table:

| Small Molecule | Range of concentrations |
| --- | --- |
| LY294002 | About 5-50 μM |
| BIO | About 1-20 μM |
| Sodium Butyrate | About 100-1000 nM |
| DMSO | About 0.1%-2% |
| SB431542 | About 0.1-20 μM |

In one example, the method as described herein may be performed by the method as summarized in FIG. 1 (left column). In one example, the compounds as used in the Example section (as summarized in FIG. 1 (left column)) may include, the components as listed in the following table and may be provided in the amount as provided in the following table:

| Small Molecule | Total amount used+ (ng) |
| --- | --- |
| Activin A | About 100-600 |
| LY294002 | About 10,000-15,000 |
| BIO | About 1000-4000 |
| Sodium Butyrate | About 50-200 |
| DMSO* | About 50-150 |
| SB431542 | About 200-500 |

*Amount of DMSO used is in µl.
+Amount of each factor used may be calculated based on the concentration of the factor used (detailed in Materials and Methods section above) and volume of 1 ml or 2 ml for a 6-well plate depending on whether full or half-medial change was performed. For example, on day 0, Activin A was added at a concentration of 100 ng/ml in 2 ml of media (i.e. amount of Activin A used = 200 ng). On day 2 and 4, 1 ml media was exchanged with fresh media containing Activin A and hence 100 ng of Activin was used on each of these days. Therefore, total usage of Activin A was 400 ng.

In one example, the method as described herein may be performed by the method as summarized in FIG. 1 (left column). In one example, the compounds as used in the Example section (as summarized in FIG. 1 (left column)) may include, the components as listed in the following table and may be provided in the amount as provided in the following table:

| Small Molecule | Total amount used+ (ng) |
| --- | --- |
| Activin A | About 400 |
| LY294002 | About 12,300 |
| BIO | About 2580 |
| Sodium Butyrate | About 110 |
| DMSO* | About 70 |
| SB431542 | About 384 |

*Amount of DMSO used is in µl.
+Amount of each factor used may be calculated based on the concentration of the factor used (detailed in Materials and Methods section above) and volume of 1 ml or 2 ml for a 6-well plate depending on whether full or half-medial change was performed. For example, on day 0, Activin A was added at a concentration of 100 ng/ml in 2 ml of media (i.e. amount of Activin A used = 200 ng). On day 2 and 4, 1 ml media was exchanged with fresh media containing Activin A and hence 100 ng of Activin was used on each of these days. Therefore, total usage of Activin A was 400 ng.

In one example, in order to confirm that an induced cell is hepatocyte-like, a combination of the following characterizations may be used:
1) Morphological analysis: typical hepatocyte morphological features such as polygonal shape, granular cytoplasm and distinct nuclei;
2) Gene expression levels of hepatic markers such as alpha feto protein (AFP) albumin (ALB) as well as cytochrome P450 enzymes (CYPs);
3) Functional assays: albumin and urea production;
4) Functional activity of CYPs; and/or
5) Drug testing applications.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or examples of the invention are described in terms of Markush groups, those skilled in the art will recognize that the invention is also thereby described in terms of any individual member or subgroup of members of the Markush group.

EXPERIMENTAL SECTION

Materials and Methods
hESC Cell Culture
hESC cell line, H9 (WiCell Research Institute, Madison, Wis.) was cultured and propagated on tissue culture plates coated with matrigel (BD Biosciences, San Jose, Calif., USA) in mTeSR™ 1 media (Stem Cell Technologies, Vancouver, BC, Canada). Cultures were passaged at intervals of 5-7 days by incubation with 1 mg/ml dispase (Stem Cell Technologies) for 5 minutes at 37° C. Colonies were picked under microscopic guidance and replated at 1:3 to 1:6 split ratios.
PHHs Culture
Cryopreserved PHHs were obtained from Life Technologies (Carlsbad, Calif., USA) and BD Biosciences (Franklin Lakes, N.J., USA). The cells were thawed in a 37° C. water bath and resuspended in pre-warmed InVitroGRO HT Thawing Medium (Celsis, In Vitro Technologies, Baltimore, Md., USA). The cells were centrifuged at 800 rpm at 4° C. and the cell pellet was resuspended in InVitroGRO CP Plating Medium (containing 0.02% Torpedo Antibiotic Mix). Cells were counted and 50,000 cells were plated into each well of 96-well plates (Nunc, Naperville, Ill., USA) pre-coated with neutralized 1.5 mg/ml PureCol® Bovine Collagen solution, Type 1 (Advanced Biomatrix, San Diego, Calif., USA). After allowing for cell attachment for 4 hours, the media was changed to William's media E (Sigma-Aldrich, Singapore), supplemented with 1 mg/ml bovine serum albumin (Sigma), 1× insulin-transferrin-selenium and 1×MEM non-essential amino acids (Gibco, Carlsbad, Calif., USA), 100 nM dexamethasone (Sigma), 0.3 mg/ml L-glutamine (Lonza, Basel, Switzerland), 100 U/ml penicillin and 100 µg/ml streptomycin (Cellgro, Manassas, Va.). Culture medium was changed daily. Three different lots of hepatocytes were used for the experiments. All assays were performed after 2 days of culture.
In Vitro Differentiation
The differentiation was initiated when hESCs reached a confluence level of approximately 80%. All differentiations were done in 24 or 48 well plates (Nunc, Naperville, Ill., USA) pre-coated with matrigel diluted in Dulbecco's Modified Eagle Medium: Nutrient Mixture F-12 (DMEM/F12, Gibco) for 1-2 h at 37° C., in a 5% $CO_2$ atmosphere. To induce differentiation, expansion medium was switched to basal differentiation medium, sequentially supplemented with either growth factor or small molecule cocktails as described in FIG. 1 for 20 days. Media contained 2% fetal bovine serum (FBS, HyClone, Thermo Scientific, Logan, Utah) between days 1-6 and 0.5% FBS between days 6-20. The growth factor based differentiation was adopted from the protocol developed by Roelandt et al, PloS One 5 (2010) e12101, the content of which is incorporated herewith by reference. Briefly, basal differentiation medium was composed of 60% DMEM-low glucose (Gibco, Carlsbad, Calif., USA), 40% MCDB-201-water (Sigma), 0.25× Linoleic acid—Bovine serum albumin (LA-BSA) (Sigma), 0.25× Insulin-transferrin-selenium (ITS) (Sigma), 100 U/mL Penicillin and 100 µg/mL Streptomycin (Cellgro), 0.1 mM L-Ascorbic Acid (Sigma), 1 µM Dexamethasone (Sigma) and 110 µM 2-mercaptoethanol (Gibco). The following cytokines and growth factors (all from R & D Systems, Minneapolis, Minn., USA) were added at different steps for differentiation: rh/m/r Activin-A (100 ng/ml), rmWnt3a (50 ng/ml), rhFGF2 (10 ng/ml), rhBMP4 (50 ng/ml), rhFGF1 (50 ng/ml), rmFGF8b (25 ng/ml), rhFGF4 (10 ng/ml), rmFollistatin-288 (100 ng/ml), rhOncostatin M (100 ng/ml), rhHGF (20 ng/ml). The following small molecules were added at different steps to the differentiation media: 5 µM IDE-2 (Stemgent, Cambridge, Mass., USA), 10 µM LY294002 (Sigma), 2 µM bromo-indirubin-3'-oxime (BIO, Sigma), 250 nM sodium butyrate (Sigma) and 1 µM 5B431542 (Calbiochem Darmstadt, Germany). In addition, DMSO (Sigma) was added in combination with sodium butyrate and 5B431542 at 0.5% and 1% respectively (FIG. 1). Media was changed every other day and half of the media was replaced with fresh media containing growth factors/ small molecules within the same step.

Quantitative Real-Time PCR (qPCR)

RNeasy Micro-kit (Qiagen, Hilden, Germany) was used For RNA isolation. The total amount of RNA was determined using a NanoDrop™ ND-1000 Spectrophotometer. cDNA synthesis was performed from 1 µg of RNA using iScript cDNA synthesis kit (Bio-Rad Laboratories, Hercules, Calif., USA). qPCR was conducted using a 7000 Fast Real-Time PCR System (Applied Biosystems, Foster City, Calif., USA). Primers were obtained commercially from GeneCopoeia, Inc. (Rockville, Md., USA). The expression levels of all marker genes were normalized to the expression levels of glyceraldehyde-3-phosphate dehydrogenase (GAPDH) to account for differences in cell numbers.

Immunofluorescence

Immunostaining was performed as described previously, in N. Sadoni et al, J. Cell Biol 146 (1999); 1211-1226, the content of which is incorporated herewith by reference. The following primary antibodies were used: mouse anti-AFP (Sigma), goat anti-Albumin (Alb; Abcam, Cambridge, UK), mouse anti-SOX17 (Abcam) and rabbit anti-FOXA2 (Abcam). Alexa Fluor 488-conjugated anti-rabbit (Invitrogen) and Alexa Fluor 555-conjugated anti-mouse (Invitrogen) secondary antibodies were applied. Cell nuclei were stained with DAPI and imaging was performed with Olympus BX-DSU microscope (Olympus, Tokyo, Japan).

Albumin Secretion and Urea Production

Albumin secretion was measured using a human albumin enzyme-linked immunosorbent assay (ELISA) quantitation kit quantification kit (Bethyl Laboratories, Inc., Montgomery, Tex., USA) as per manufacturer's protocol.

Urea production was measured using Direct Urea Nitrogen Color Reagent and Direct Urea Nitrogen Acid Reagent (Standbio Laboratory, Boerne, Tex., USA). Briefly, the supernatant from cell culture media was heated with a 2:1 mixture of acid reagent: color reagent at 90° C. for 30 minutes. The reaction was stopped by cooling on ice and the optical density was measured at 520 nm.

All functional data was normalized to the number of cells seeded which was quantified using the Quant-iT PicoGreen dsDNA Assay Kit (Invitrogen, Singapore).

Cytochrome P450 Activity

Basal and induced activity of CYP450 enzymes was determined using specific inducers (CYP1A2: 40 µM β-naphthaflavone, CYP3A4: 20 µm rifampicin, CYP2B6: 200 µM phenobarbital) and substrates (CYP1A2: 200 µM phenacetin, CYP3A4: 5 µM midazolam, CYP2B6: 1000 µM bupropion). The inducers and substrates were obtained from Sigma. For measuring basal activity, at the end of the 20-day differentiation period, medium was removed and the cells were incubated for 2 h at 37° C. with Krebs-Henseleit bicarbonate (KHB) buffer containing specific CYP substrates. The drug metabolite product in the supernatant was analyzed by Liquid Chromatography-Mass Spectrometry (LC-MS Finnigan LCQ Deca XP Max, Agilent 1100 series) according to procedures described previously in B. Nugraha, et al., Biomaterials 32 (2011), 6982-6994, the content of which is incorporated herewith by reference. For induction studies, at the end of the 20-day differentiation period, cells were cultured in medium containing CYP-specific inducers for 48 hours. Fold induction was measured by gene expression levels before and after induction. Induction levels were confirmed by LC-MS.

Cell Viability Assays

Cell viability of differentiated hepatocytes was measured 24 hours after treatment with drugs using CellTiter 96® Non-Radioactive Cell Proliferation Assay (MTT) (Promega, Madison, Wis., USA) according to manufacturer's instructions. The following drugs were used for the cell viability assays: Acetaminophen, Diclofenac, Digoxin, Chlorpromazine, Troglitazone and Quinidine (all drugs from Sigma). Stock solutions of drugs were prepared in DMSO and then diluted in media to obtain desired working concentrations. Controls were treated with DMSO alone (in absence of test compounds) and considered as 100% viability value.

Statistical Analysis 3 independent batches of differentiation for hESC derived hepatocytes and 3 independent lots (donors) for PHHs were used. In each independent experiment, treatments were repeated in duplicate. Statistical comparisons were undertaken using unpaired Student's t test. Results are expressed as mean±standard error of the mean (sem) of 3 independent experiments.

Example 1—Initial Results

The 3-step small molecule based differentiation strategy is outlined in FIG. 1 (left-hand column). The results from stages of differentiation were compared to the 4-step growth factor based differentiation strategy as known in the art (FIG. 1, right hand column).

Differentiation of hESCs to Definitive Endoderm

In human embryonic stem cells (hESCs), manipulations of Nodal and Wnt signaling have been exploited to direct differentiation towards definitive endoderm (DE). Activin A activates the Nodal pathway and directs definitive endoderm formation while a synergistic activation of Nodal and Wnt-β catenin signaling promotes more efficient generation of definitive endoderm (DE) from human embryonic stem cells (hESCs). Therefore, to induce differentiation of HESCs into definitive endoderm using small molecules, the present study analyzed effects of compounds which could substitute for Activin A or/and Wnt signaling. These compounds include 1) IDE-2, a small molecule which has been reported to induce definitive endoderm (DE) differentiation of human embryonic stem cells (hESCs), 2) bromo-indirubin-3'-oxime (BIO), a glycogen synthase kinase 3 (GSK-3) inhibitor (GSK-3 inhibition mimics activation of Wnt signaling), 3) LY294002, which has been reported to inhibit insulin, insulin growth factor and FGF-mediated phosphoinositide3 kinase (PI3K)-AKT signaling pathway that acts to maintain pluripotency and has been shown to promote differentiation to definitive endoderm (DE). Cells were cultured in the presence of diverse combinations of these three compounds for 6 days, and expression of pluripotency marker (OCT4) and definitive endoderm markers (SOX17 and FoxA2) were analyzed using qPCR. Growth factor based differentiation using Activin A and Wnt 3a was used as control.

Figure 2:
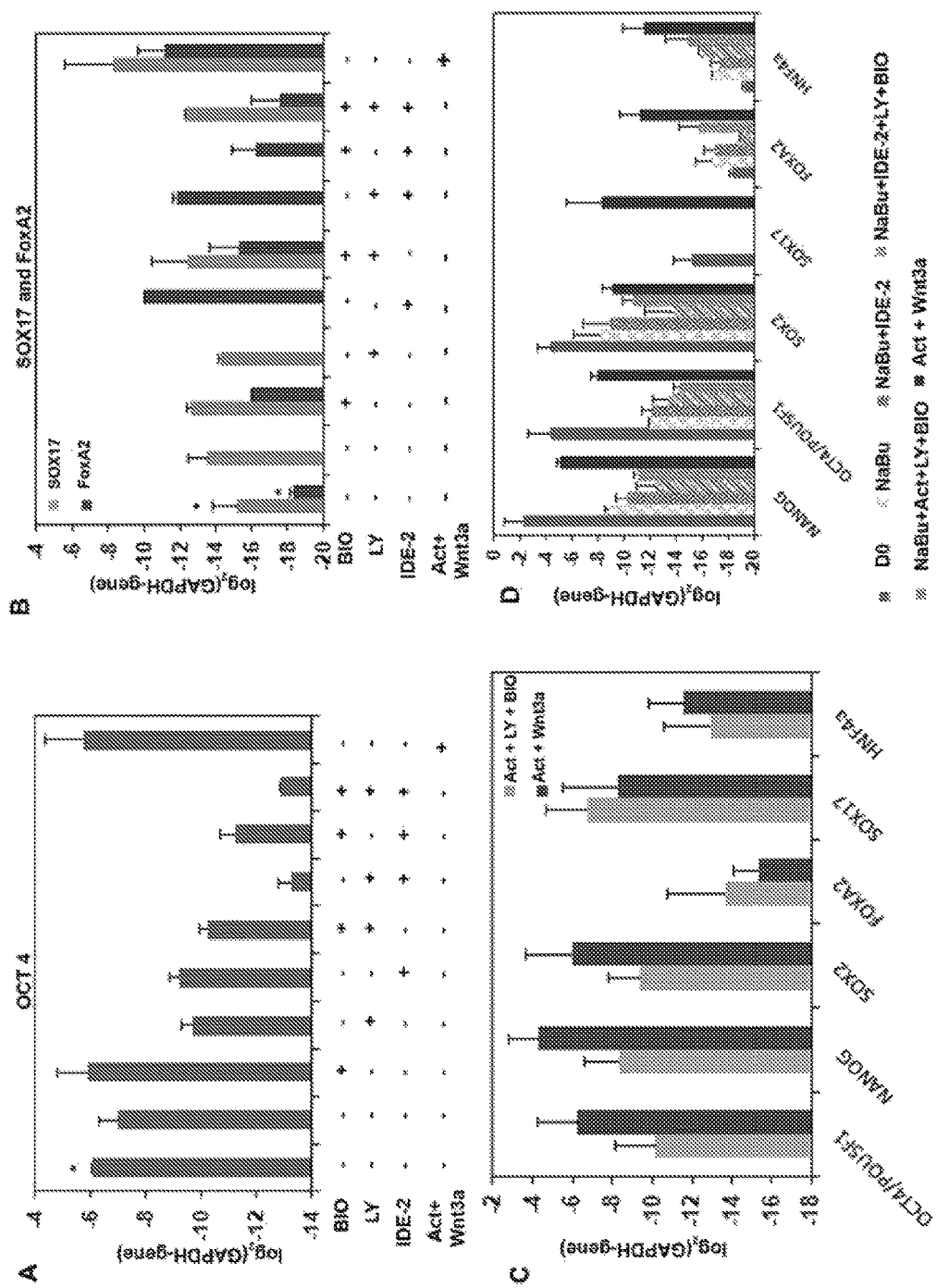
FIG. 2 shows the bar graphs illustrating the results of qPCR analysis of Activin A and Wnt3a replacement on the induction of definitive endoderm. Expression of pluripotent marker OCT4 (A) and definitive endoderm markers FoxA2 and SOX17 (B) in human embryonic stem cells (hESCs) treated for 6 days with small molecules in different combinations or with growth factors. *The first bar in A and B represent marker expression at Day 0. Second Bar represents marker expression at Day 6 without any small molecule or growth factor treatment (Cells were treated with DMSO as vehicle control for small molecules). (C) Expression of HNF4α, pluripotent markers OCT4, Nanog and SOX2 and definitive endoderm markers FoxA2 and SOX17 in human embryonic stem cells (hESCs) treated with a combination of Activin and small molecules (grey bars) in comparison to hESCS treated with Activin A and Wnt3a. (D) Gene expression of day-6 differentiated cells with different small molecule treatment in combination with epigenetic modulator. Expression levels were compared to growth-factor differentiated cells (dark grey bars) and cells differentiated with growth factor, small molecules and epigenetic modulator (light grey bar with white dots). Results are plotted relative to GAPDH. Bars show average±s.d (n=3).

It is shown that that cells treated with Activin A and Wnt 3a induced the expression of endoderm markers FoxA2 and SOX17, but pluripotency marker OCT4 remained expressed (FIG. 2 A, B). In contrast, treatment with small molecules (except for treatment with BIO alone) was more efficient in downregulating the expression of pluripotency marker (FIG. 2A), in particular treatment with IDE-2 and LY294002 and a combination of IDE-2, LY294002 and BIO. However, treatment with these compounds did not induce expression of definitive endoderm markers (such as FoxA2 and SOX17) at levels compared to Activin A and Wnt3a treatment (see FIG. 2B). Out of the combinations of small molecules, treatment with LY294002 and BIO and with IDE-2, LY294002 and BIO led to highest induction of SOX17 while treatment with IDE-2 induced the highest FoxA2 expression. Taken together, these results suggested that treatment with the small molecules helped in suppression of pluripotency but was not sufficient to induce DE differentiation without the presence of Activin A.

Since treatment with a combination of IDE-2, LY294002 and BIO showed both downregulation of OCT4 and comparable expression of SOX17 compared to other combinations of small molecules, it was tested whether substitution of IDE-2 with Activin A could downregulate pluripotency markers more efficiently than treatment with Activin A and Wnt3a and also induce definitive endoderm differentiation. It was observed in the present study that combination of Activin A, LY294002 and BIO showed lower expression of pluripotency markers OCT4, Nanog and SOX2 and similar expression of FoxA2, SOX17 and Hnf4α compared to Activin A and Wnt3a treated cells (FIG. 2C).

In addition to the compounds above, the effect of epigenetic modulation on definitive endoderm (DE) differentiation of human embryonic stem cells (hESCs) was also investigated. Sodium butyrate has been reported to be a histone deacetylase inhibitor, which in turn is known to induce differentiation of a number of cells types. However, the role of sodium butyrate in hepatocyte differentiation protocols is controversial. Sodium butyrate has been reported to contribute to more homogenous hepatocyte differentiation, although other reports showed that sodium butyrate alone was not sufficient for DE induction or hepatocyte differentiation. Therefore, the effects of sodium butyrate alone or in combination with IDE-2 on the endodermal differentiation of HESCs were investigated here. In addition, effects of IDE-2 and sodium butyrate in combination with LY294002 and BIO were also tested. Since combination of LY294002, BIO and Activin A showed the most optimal downregulation of pluripotent markers and expression of DE markers in the preliminary screening, this condition was also included. It is shown herein that none of these combinations except for Activin A in combination with LY294002 and BIO (FIG. 2C) resulted in expression of definitive endoderm (DE) markers such as FoxA2 and SOX17 (FIG. 2D). This suggests that Activin A is indispensable for differentiation of hESCs into definitive endoderm. These findings are consistent with previous reports where Activin was an absolute requirement even when other factors, such as LY294002 or sodium butyrate were used for differentiation of human embryonic stem cells (hESCs) to definitive endoderm (DE).

In summary, treatment with small molecules was effective in more efficient downregulation of pluripotency markers but was not sufficient to induce DE induction without the addition of Activin A. Combination of Activin A and small molecules, LY294002 and BIO resulted in downregulation of pluripotency markers and upregulation of definitive endoderm (DE) markers. In addition, this combination could be more a promising condition for definitive endoderm (DE) induction compared to growth factor (Activin A and Wnt3a) treatment due to more effective downregulation of pluripotency. Hence, for subsequent small-molecule based steps to generate hepatoblasts and hepatocytes, combination of Activin A, LY294002 and BIO was used for the first stage of definitive endoderm induction (FIG. 1).

Initiation of Hepatic Differentiation from Definitive Endoderm

Figure 3:
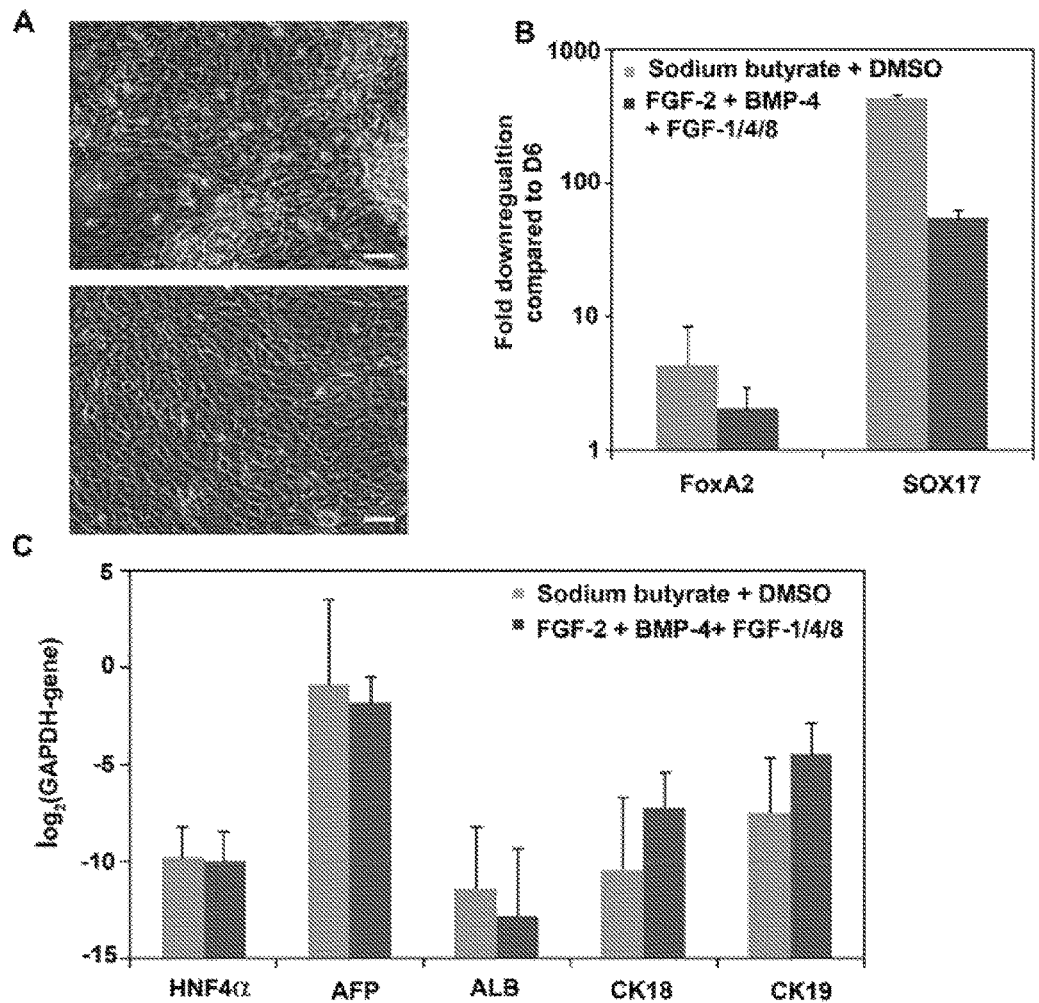
FIG. 3 shows the results in the analysis on whether small molecules efficiently induce formation of hepatoblasts from definitive endoderm. In particular, (A) shows phase contrast images showing morphology of cells in definitive endoderm stage induced for additional 6 days with small molecules-sodium butyrate and DMSO (upper panel) or for 8 days with growth factors-FGF-2, BMP-4 and consecutively FGF-1, FGF-4 and FGF-8 (lower panel). Scale bar: 250 μm; (B) shows a bar graph depicting the results of qPCR analysis showing downregulation of definitive endoderm markers FoxA2 and SOX17 in cells treated with small molecules or growth factors. Expression levels of FoxA2 and SOX17 are expressed relative to Day 6. Bars show average±s.d (n=3); (C) shows a bar graph depicting the results of qPCR analysis showing hepatic markers AFP, Alb and HNF4α, CK18 and biliary marker CK19 confirming the generation of hepatoblasts in cells treated with small molecules or growth factors. Results are plotted relative to GAPDH. Bars show average±s.d (n=3). Thus.

In the second stage of one of the differentiation method as described herein, the effect of sodium butyrate and DMSO on the initiation of hepatic differentiation was analysed. After 6 days of sodium butyrate and DMSO treatment, the morphology of the definitive endoderm (DE) cells resembled cuboidal shapes typical of hepatocytes (FIG. 3A, upper panel). This morphology was consistent in both the growth factor (4 days induction with FGF-2 and BMP-4 and consecutive additional 4 days with FGF-1, 4 and 8, FIG. 1) and small molecule differentiated cells (FIG. 3A, lower panel). In order to monitor the transition of the cells from definitive endoderm (DE) to hepatic progenitors, the gene expression levels of definitive endoderm (DE) markers (such as FoxA2 and SOX17) and hepatic markers alpha fetoprotein (AFP), albumin (Alb) and hepatocyte nuclear factor (HNF) 4α were quantified by qPCR. In both growth factor and small molecule induced hepatic differentiation, there was reduction in definitive endoderm markers (such as FoxA2 and SOX17) compared to levels quantified in the definitive endoderm (DE) stage (FIG. 3B). In addition, hepatic marker expression of cells treated with sodium butyrate and DMSO were comparable to the growth factor-based differentiation (FIG. 3C). No significant differences were observed between the levels of AFP, Alb and HNF4α. At this stage, albumin production was not detected, indicating that most of these cells are early hepatic cells (data not shown). During liver development, hepatocytes and cholangiocytes have been suggested to be derived from a common progenitor, namely, hepatoblasts. The qPCR results showed expression of hepatocyte markers such as albumin and cytokeratin 18 (CK18) as well as cholangiocytes marker CK19 (FIG. 3C). This was applicable for growth-factor based as well as small molecule based initiation of hepatic differentiation, although levels of CK 18 and CK19 were lower in small molecule based differentiation. Altogether, these results suggest that hepatoblasts had been generated during the differentiation process and that small-molecule-based induction was comparable to the growth factor based induction.

Maturation of Hepatic Cells

In the third stage, SB431542, a TGFβ inhibitor and DMSO was used to promote the maturation of early hepatic cells (FIG. 1). DMSO has been reported to promote maturation of fetal liver cells. However, whether maturation using DMSO can direct hepatoblasts to mature hepatocytes without any tendency for cells to differentiate towards cholangiocytes is not well documented. On the other hand, it has been shown that TGFβ signaling gradient promotes biliary differentiation. Therefore, the effect of a combination of DMSO and TGFβ inhibitor treatment on hepatic maturation and at the same time prevent maturation of biliary lineage was observed. After 8 days of treatment with SB431542 (TGFβ inhibitor) and DMSO, expression of hepatocyte markers was analyzed by qPCR. The results of the small molecule-induced maturation were compared to the maturation process induced by growth factors (6 days treatment with HGF and Follistatin). Cells matured using both approaches showed expression of hepatic markers that have been previously been shown to be expressed at the second stage of differentiation, including AFP, Alb, CK18 and HNF4α (FIG. 4A). Decrease in levels of AFP and increase in levels of Alb, compared to the second stage of differentiation confirmed the maturation of the hepatic cells (FIGS. 4A and 3C). Furthermore, the cells also expressed mature hepatocyte markers HNF4α, alpha-1-antitrypsin (AAT), asialoglycoprotein receptor (ASGPR) and multidrug resistance protein 2 (MRP2), as well as cytochrome P450 enzymes, CYP3A4, CYP1A1 and CYP1A2 (FIG. 4A). Hepatocytes generated using predominantly small molecules based approach are hereafter referred to as small molecule-derived hepatocytes (or SM-Hep) and hepatocytes generated using the growth factor approach are referred to as growth factor-derived hepatocytes (or GF-Hep).

Functional Activity of Differentiated Hepatocytes

To test whether the hepatocytes generated using the small molecule approach possess liver specific functions, urea and albumin production of these cells were measured (FIG. 5A, B) Small molecule-derived hepatocytes (SM-Hep) produced 0.15 pg/48 hours/cell albumin which was similar, although slightly lower, to that of growth factor-derived hepatoctyes (GF-Hep) (FIG. 5A). In contrast, urea production in small molecule-derived hepatocytes (SM-Hep) was higher than that of growth factor-derived hepatocytes (GF-Hep) (FIG. 5B).

The activity levels of CYP enzymes in small molecule-derived hepatocytes (SM-Hep) were compared to that of growth factor-derived hepatoctyes (GF-Hep) according to the metabolism of CYP1A2 and CYP3A4 substrates (FIG. 5C). The activity levels of CYP1A2 and CYP3A4 were comparable in hepatocytes differentiated using the two approaches (FIG. 5).

Drug-Induced Cytotoxicity of Differentiated Hepatocytes

One of the major applications of hepatocytes is toxicity screening in order to aid drug development and discovery. Researchers have tried to predict drug-induced cytotoxicity in vitro using HepG2, HepaRG primary human hepatocyte (PH) as well as hESC/hiPSC-derived hepatocyte like cells. Although primary human hepatocyte (PH) are considered the gold standard for drug metabolism and toxicity in vitro, cells lines such as HepG2 and HepaRG are less expensive than primary human hepatocyte (PH) and reproducible experiments are easier to perform than they are with primary human hepatocyte (PHs). However, 30% of the compounds were incorrectly classified as nontoxic. To overcome these problems, it would be highly advantageous if hESC/hiPSC derived hepatocytes could be used to predict drug-induced toxicity. To examine its applicability to drug screening, small molecule-derived hepatocytes (SM-Hep) were treated with various drugs that cause hepatotoxicity. Cell viability, assessed using MTT assay, was compared to growth factor-derived hepatoctyes (GF-Hep) as well as primary human hepatocyte (PH). The susceptibility of small molecule-derived hepatocytes (SM-Hep) to all the drugs tested was similar to that of the growth factor-derived hepatoctyes (GF-Hep) (FIG. 6).

The estimated $IC_{50}$ of the drugs for small molecule-derived hepatocytes (SM-Hep) and growth factor-derived hepatoctyes (GF-Hep) were compared. As shown in Table 1, there was no significant difference in the $IC_{50}$ of the drugs when growth factor-derived hepatoctyes (GF-Hep) and small molecule-derived hepatocytes (SM-Hep) were compared. This suggests that differentiation using a small-molecule based approach doesn't affect the sensitivity of the cells to paradigm hepatotoxicants. Therefore, small molecule-derived hepatocytes (SM-Hep) can serve as a valuable tool for drug screening. The susceptibility of the differentiated hepatocytes to the drugs to that of primary human hepatocyte (PH) was also compared. The drug-induced toxicity in differentiated hepatocytes (both SM-Hep and GF-Hep) was similar to that of the primary human hepatocyte (PH) when treated with Acetaminophen, Diclofenac and Chlorpromazine (FIG. 6). There was no statistically significant difference in the $IC_{50}$ of these drugs when small molecule-derived hepatocytes (SM-Hep) and primary human hepatocyte (PH) were compared (Table 1). The $IC_{50}$ of Digoxin was similar in growth factor-derived hepatoctyes (GF-Hep), small molecule-derived hepatocytes (SM-Hep) and primary human hepatocyte (PH) (Table 1). However, the dose response curve when primary human hepatocyte (PH) were treated with Digoxin was slightly different from that of growth factor-derived hepatoctyes (GF-Hep) or small molecule-derived hepatocytes (SM-Hep) (FIG. 6). When treated with Quinidine, the viability of the primary human hepatocyte (PH) was lower than that of growth factor-derived hepatoctyes (GF-Hep) or small molecule-derived hepatocytes (SM-Hep) as shown from the dose-response curves as well as the $IC_{50}$ values (FIG. 6, Table 1). In contrast, treatment with troglitazone resulted in higher viability of primary human hepatocyte (PH) compared to growth factor-derived hepatoctyes (GF-Hep) or small molecule-derived hepatocytes (SM-Hep).

TABLE 1

$IC_{50}$ values for hepatotoxicity screening using hepatocytes differentiated using growth factors (GF) or small molecules (SM).

| | $IC_{50}$(μm) | | | Statistical Significance | |
| --- | --- | --- | --- | --- | --- |
| | GF-Hep | SM-Hep | PH | p-value[a] | p-value[b] |
| Acetaminophen | 46.0 × 10³ | 38.1 × 10³ | 45.2 × 10³ | >0.1 | 0.1 |
| Diclofenac | 1859.7 | 1927.7 | 3585.6 | >0.1 | >0.1 |
| Digoxin | 0.25 | 0.36 | 0.34 | >0.1 | >0.1 |
| Chlorpromazine | 61.3 | 66.9 | 71.8 | >0.1 | >0.1 |
| Quinidine | 538.5 | 728.2 | 198.4 | >0.1 | <0.01 |
| Troglitazone | 33.7 | 31.9 | 85.0 | >0.1 | <0.01 |

$IC_{50}$ values were compared to primary hepatocytes (PH). P-values[a] indicate significant statistical differences between IC$_{50}$ values in GF-Hep and SM-Hep. P-values[b] indicate significant statistical differences between IC$_{50}$ values in SM-Hep and PH.

In summary, the present data provides an example of a step-wise protocol for differentiating hESCs into functional hepatocytes using predominantly small molecules. As mentioned earlier, large amounts of cells are needed for applications of hepatocytes in cell therapy and hepatotoxicity screening. Hence, a cost-effective way of generating functional hepatocytes can result in valuable impact in the industry. In one example, the present approach allows a 67% reduction in cost of hepatocyte generation compared to the conventional growth factor approach. The reduction in cost is even more significant when compared with primary human hepatocytes (81%). Based on these calculations, in a pharmaceutical setting for drug testing where large scale screening of compounds would need hundreds of well plates, the cost savings could be enormous. For example, if 100 plates (384-well plate format) were to be used, the cost savings would be approximately 7500 dollars per set of experiments if our approach was used over the growth factor approach. If primary human hepatocytes were to be used in these settings, the cost savings of using our approach to derive hepatocytes from hESCs would be significant.

Example 2—Updated Results of Example 1 a. Differentiation of hESCs to Definitive Endoderm

In human embryonic stem cells (hESCs), manipulations of Nodal and Wnt signaling have been exploited to direct differentiation towards DE. Activin A activates the Nodal pathway and directs definitive endoderm (DE) formation while a synergistic activation of Nodal and Wnt-β catenin signaling promotes more efficient generation of definitive endoderms (DEs) from hESCs. Therefore, to induce differentiation of hESCs into definitive endoderm (DE) using small molecules, the effects of compounds which could substitute for Activin A or/and Wnt signalling were analysed. These compounds include 1) IDE-2, a small molecule which has been reported to induce definitive endoderm (DE) differentiation of hESCs, 2) BIO, a glycogen synthase kinase 3 (GSK-3) inhibitor (GSK-3 inhibition mimics activation of Wnt signaling), 3) LY294002, which has been reported to inhibit insulin, insulin growth factor and FGF-mediated phosphoinositide3 kinase (PI3K)-AKT signaling pathway that acts to maintain pluripotency and has been shown to promote differentiation to definitive endoderm (DE).

Figure 8:
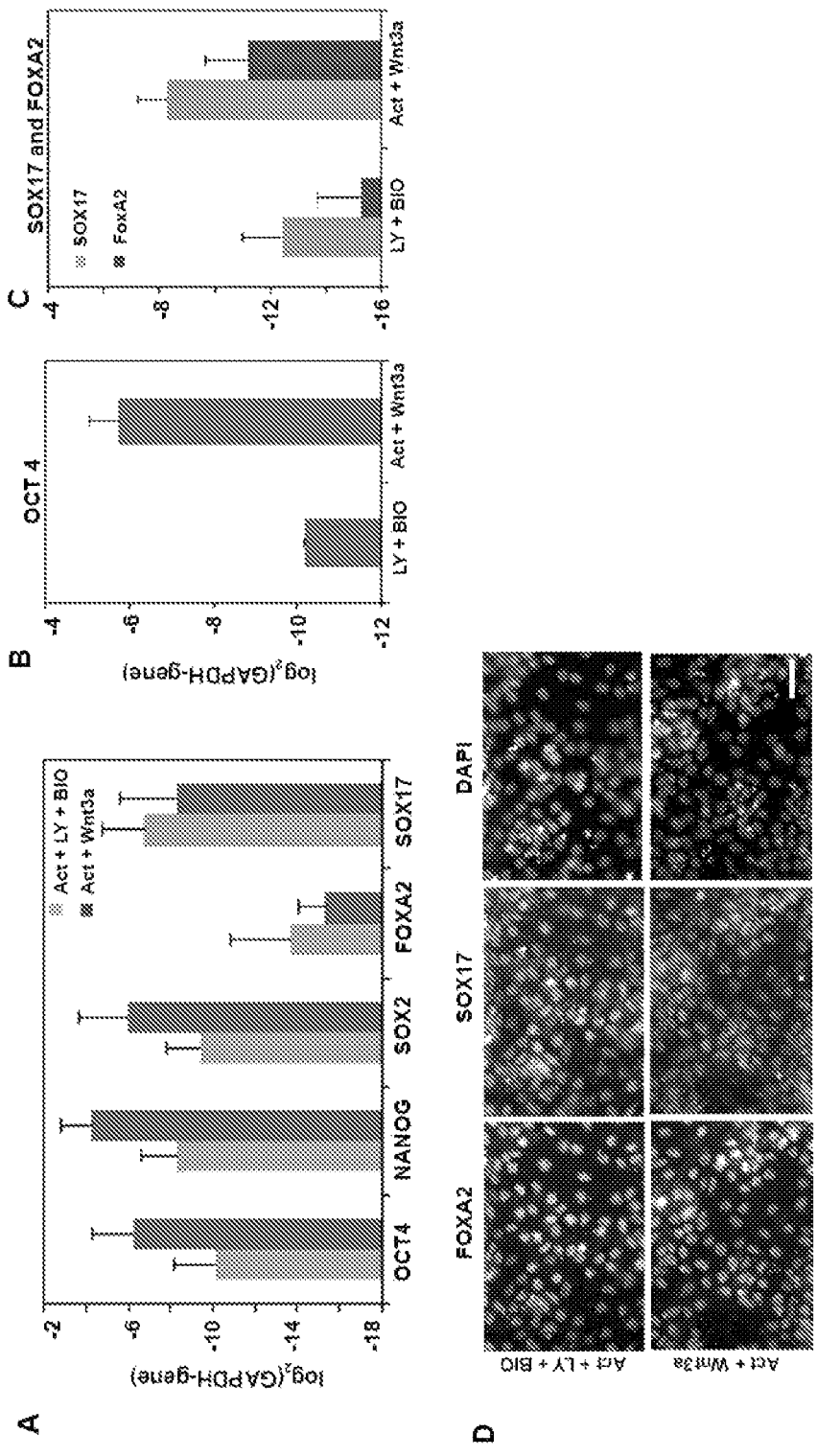
FIG. 8 shows the results of qPCR analysis, which shows the effect of Activin A and Wnt3a replacement on the induction of definitive endoderm. In particular, (A) shows the expression of pluripotent markers OCT4, Nanog and SOX2 and definitive endoderm markers FOXA2 and SOX17 in hESCs treated with a combination of Activin and small molecules (light grey bars) in comparison to hESCs treated with Activin A and Wnt3a (dark grey bars). (B), which shows the expression of pluripotent marker OCT4 and (C) which shows the expression of definitive endoderm markers FOXA2 and SOX17 in hESCs treated for 6 days with small molecules or growth factors. Results are plotted relative to GAPDH. Data are presented as mean±sem. (D) Marker protein expression of FOXA2 and SOX17 detected by immunofluorescence in DE generated using a combination of Activin and small molecules (upper panel) and compared to treatment with Activin A and Wnt3a (lower panel). Cell nuclei were stained with DAPI. Scale bar: 50 LY: LY294002; Act: Activin A; GAPDH: Glyceraldehyde 3-phosphate dehydrogenase. Thus.

First the possibility of Wnt3a could be substituted by small molecules was investigated. Since LY294002 inhibits maintenance of pluripotency and BIO mimics Wnt signaling, these two compounds would possibly have the highest potential to replace Wnt signaling. hESCs were differentiated to DE using a combination of Activin A, LY294002 and BIO for 6 days. The expression of pluripotency markers (OCT4, Nanog and SOX2) and definitive endoderm (DE) markers (SOX17 and FOXA2) were analyzed using qPCR. Growth factor based differentiation using Activin A and Wnt3a was used as control. Our results showed the expression levels of pluripotency markers OCT4, Nanog and SOX2 with Activin A, LY294002 and BIO treatment were respectively 15, 16 and 11 fold lower when compared to Activin A and Wnt3a treated cells (FIG. 8A). The results also showed that Activin A, LY294002 and BIO treatment induced similar expression of DE markers, FOXA2 and SOX17 compared to Activin A and Wnt3a treated cells (FIG. 8A). These results suggest that a combination of LY294002 and BIO can replace Wnt Signaling. In addition, treatment with these compounds suppressed pluripotency more effectively than treatment with Wnt3a.

Figure 9:
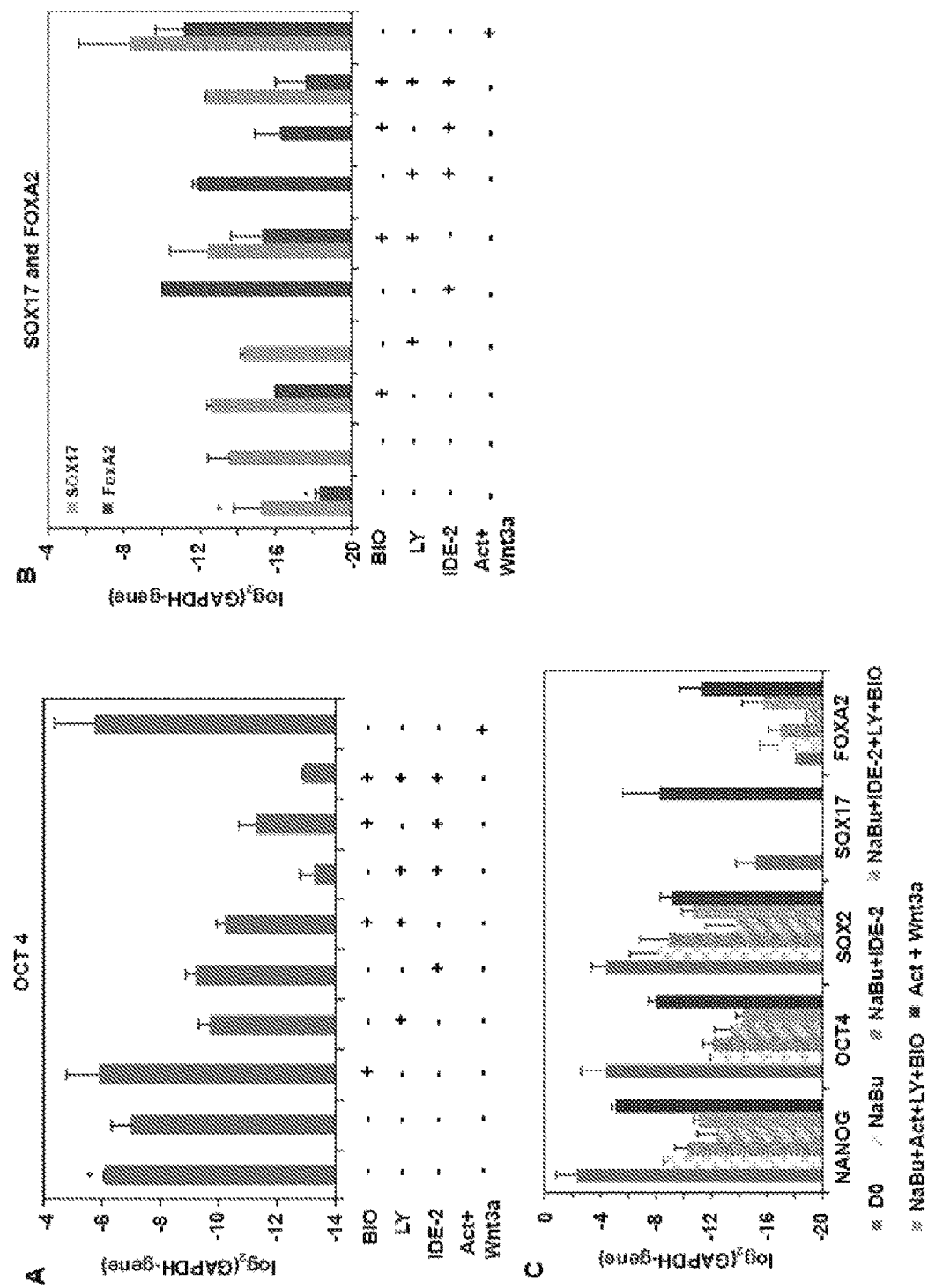
FIG. 9 shows the expression of pluripotent marker OCT4 (A) and definitive endoderm markers FOXA2 and SOX17 (B) in hESCs treated for 6 days with small molecules in different combinations or with growth factors. *The first bar in A and B represent marker expression at Day 0. Second Bar represents marker expression at Day 6 without any small molecule or growth factor treatment (Cells were treated with DMSO as vehicle control for small molecules). Effects of LY294002 and BIO, together with a small molecule replacement for Activin A, IDE-2 on the induction of hESCs into DE were tested. Effects of IDE-2, LY294002 or BIO alone or in combination with only other factor were also tested (combinations tabulated in x axis). Growth factor based differentiation using Activin A and Wnt3a was used as control. Treatment with small molecules (except for treatment with BIO alone) was more efficient in downregulating the expression of OCT4, in particular treatment with IDE-2 and LY294002 and a combination of IDE-2, LY294002 and BIO (143 and 126 fold downregulation respectively compared to day 0). Treatment with these compounds did not induce expression DE markers (FOXA2 and SOX17) at levels compared to Activin A and Wnt3a treatment. Out of the combinations of small molecules, treatment with LY294002 and BIO and with IDE-2, LY294002 and BIO led to the highest induction of SOX17 but the expression of FOXA2 for both these combinations were significantly lower when compared to Activin A and Wnt3a treated cells. Treatment with IDE-2 and with a combination of IDE-2 and LY94002 induced the highest FOXA2 expression (almost comparable levels to Activin A and Wnt3a treatment). However, no SOX17 expression was detected for these combinations. (C) Gene expression of day 6 differentiated cells with different small molecule treatment in combination with epigenetic modulator. Expression levels were compared to growth-factor differentiated cells (dark grey bars) and cells differentiated with growth factor, small molecules and epigenetic modulator (light grey bar with white dots). None of these combinations resulted in expression of DE markers, FOXA2 and SOX17 to levels comparable to Activin A and Wnt3a treatment. Results are plotted relative to GAPDH. Data are presented as mean±sem. NaBu: sodium butyrate; LY: LY294002; Act: Activin A; GAPDH: Glyceraldehyde 3-phosphate dehydrogenase. Thus.

Next, the possibility if LY294002 and BIO could also replace Activin A for induction of hESCs into definitive endoderm (DE) was also examined. Growth factor based differentiation using Activin A and Wnt3a was used as control. The results showed that cells treated with Activin A and Wnt3a induced the expression of endoderm markers FOXA2 and SOX17, but pluripotency marker OCT4 remained expressed (FIG. 8B, C). In contrast, treatment with small molecules was more efficient in downregulating the expression of OCT4 (FIG. 8B). However, treatment with these compounds did not induce expression definitive endoderm (DE) markers (FOXA2 and SOX17) at levels compared to Activin A and Wnt3a treatment (FIG. 8C). In order to explore other methods of replacing Activin A signaling, the following effects are tested: of 1) IDE-2, a small molecule agonist for Activin A and 2) sodium butyrate, a histone deacetylase inhibitor, which is known to induce differentiation of a number of cells types. These two factors were tested alone or in combination with LY294002 and BIO (combinations tabulated in FIG. 9). The results (detailed in FIG. 9) showed that none of these combinations were effective in replacing Activin A signaling.

Taken together, the results show that treatment with the small molecules alone helped in suppression of pluripotency and could replace Wnt signaling but was not sufficient to induce definitive endoderm (DE) differentiation without the addition of Activin A. LY294002 and BIO only in combination with Activin A could result in definitive endoderm (DE) induction (FIG. 8A). The efficiency of definitive endoderm (DE) differentiation was confirmed by marker protein expression of FOXA2 and SOX17 (FIG. 8D). The results showed that most cells were positive for both FOXA2 and SOX17 when definitive endoderm (DE) was induced using Activin A, LY294002 and BIO (upper panel) and these results were comparable to the Activin A and Wnt3a treated cells (lower panel). This confirms the gene expression data showing that treatment with Activin A, LY294002 and BIO is equally efficient in definitive endoderm (DE) induction when compared to Activin A and Wnt3a treatment. The combination of Activin A, LY294002 and BIO could be a more promising condition for DE induction compared to growth factor (Activin A and Wnt3a) treatment due to more effective downregulation of pluripotency. Hence, for subsequent small-molecule based steps to generate hepatoblasts and hepatocytes, combination of Activin A, LY294002 and BIO was used for the first stage of DE induction (FIG. 1).

b. Initiation of Hepatic Differentiation from Definitive Endoderm

Figure 10:
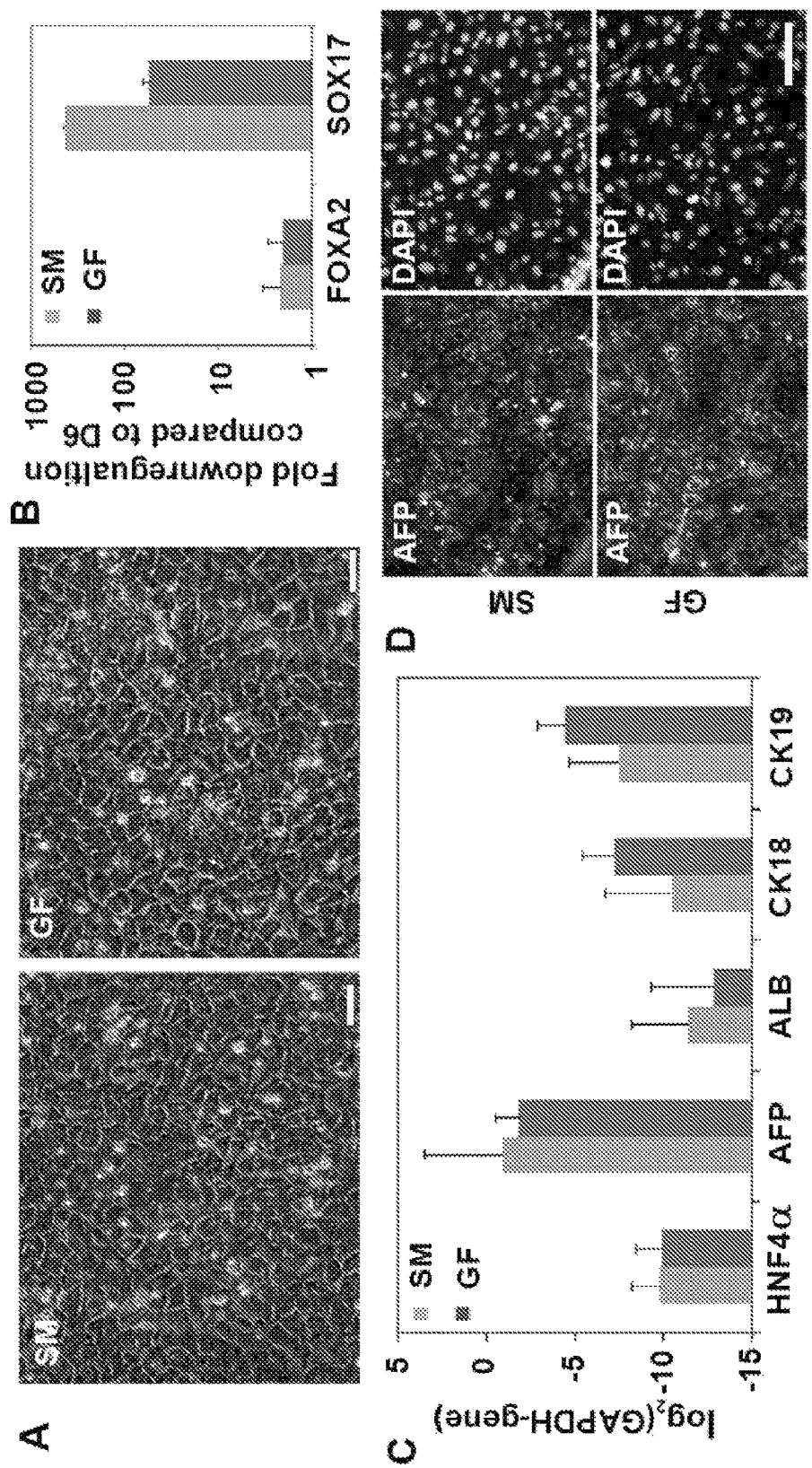
FIG. 10 shows small molecules efficiently induce formation of hepatoblasts from definitive endoderm. In particular, (A) shows phase contrast images showing morphology of cells in definitive endoderm stage induced for additional 6 days with small molecules-sodium butyrate and DMSO (left panel) or for 8 days with growth factors-FGF-2, BMP-4 and consecutively FGF-1, FGF-4 and FGF-8 (right panel). Scale bar: 25 μm. (B) shows qPCR analysis showing downregulation of definitive endoderm marker SOX17 and no downregulation in FOXA2 (p value >0.1 when compared to Day 6 levels) in cells treated with small molecules (light grey bars) or growth factors (dark grey bars). Expression levels of FOXA2 and SOX17 are expressed relative to Day 6. (C) qPCR analysis showing hepatic markers AFP, Alb and HNF4α, CK18 and biliary marker CK19 confirming the generation of hepatoblasts in cells treated with small molecules (light grey bars) or growth factors (dark grey bars). Results are plotted relative to GAPDH. Data are presented as mean±sem. (D) Marker protein expression of AFP detected by immunofluorescence in hepatoblasts generated using small molecules (upper panel) and compared to treatment with growth factor control (lower panel). Cell nuclei were stained with DAPI. Scale bar: 100 µm. SM: DE differentiated to hepatoblasts using sodium butyrate and DMSO; GF: DE differentiated to hepatoblasts using FGF-2, BMP-4 and FGF-1/4/8. Thus.

Sodium butyrate, particularly in combination with dimethyl sulfoxide (DMSO) has been reported for promoting hepatocyte differentiation. In the second stage of our differentiation method, the effect of sodium butyrate and DMSO on the initiation of hepatoblast differentiation was analysed. After 6 days of sodium butyrate and DMSO treatment, the morphology of the cells resembled cuboidal shapes typical of hepatocyte precursors (FIG. 10A, left panel). This morphology was consistent in both the growth factor (4 days induction with FGF-2 and BMP-4 and consecutive additional 4 days with FGF-1, 4 and 8, FIG. 1) and small molecule differentiated cells (FIG. 10A). In order to monitor the transition of the cells from definitive endoderm (DE) to hepatic progenitors, the gene expression levels of definitive endoderm (DE) markers FOXA2 and SOX17 and hepatic markers FOXA2, AFP, Alb and hepatocyte nuclear factor (HNF) 4a were quantified by qPCR. In both growth factor and small molecule induced hepatic differentiation, there was reduction in DE marker SOX17 compared to levels quantified in the definitive endoderm (DE) stage (FIG. 10B). The fold reduction of SOX17 was higher in the small molecule induced hepatic differentiation (440 fold) when compared to the growth factor induced hepatic differentiation (55 fold). There was no significant reduction in FOXA2 expression which is expected since FOXA2 is expressed in DE cells as well as hepatic cells.

The hepatic marker expression of cells treated with sodium butyrate and DMSO were comparable to the growth factor-based differentiation (FIG. 10C). No significant differences were observed between the levels of AFP, Alb and HNF4α. At this stage, albumin production was not detected, indicating that most of these cells are early hepatic cells (data not shown). During liver development, hepatocytes and cholangiocytes have been suggested to be derived from a common progenitor, namely, hepatoblasts. The qPCR results showed expression of hepatocyte markers such cytokeratin 18 (CK18) as well as cholangiocyte marker CK19 (FIG. 10C). This was applicable for growth-factor based as well as small molecule based initiation of hepatic differentiation. This suggests that the definitive endoderm (DE) cells were differentiated into hepatoblasts, which comprised of both hepatocytes and cholangiocytes. The efficiency of hepatobalst differentiation was examined by marker protein expression of AFP (FIG. 10D). The results showed that both growth factor and small molecule induced hepatoblast differentiation generated cells expressing AFP at comparable levels, confirming the ability of small molecules to generate hepatoblasts efficiently. These results altogether show that the cells in the definitive endoderm (DE) stage could be differentiated into hepatic progenitors using sodium butyrate and DMSO, without the use of any growth factors.

c. Differentiation of Hepatocytes from Hepatic Progenitors

Figure 11:
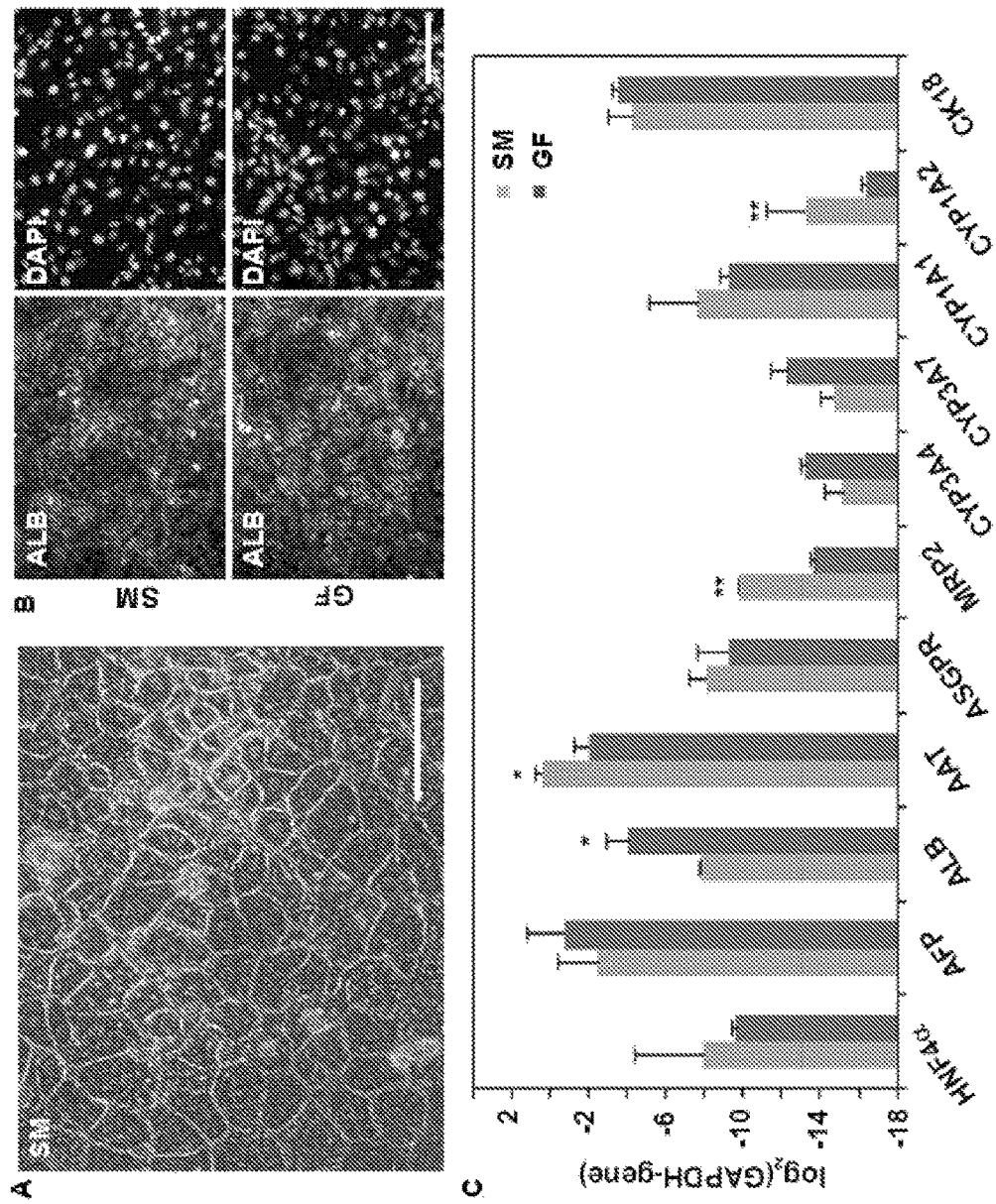
FIG. 11 shows the characterization of hepatocyte-like cells derived from hESCs using small molecules. In particular, (A) shows morphology of small molecule-derived hepatocyte-like cells showing polygonal shape and granular cytoplasm. Scale bar: 50 µm (B) shows marker protein expression of Alb detected by immunofluorescence in hepatocytes generated using small molecules (upper panel) and compared to treatment with growth factor control (lower panel). Scale bar: 100 µm. (C) shows expression of hepatic markers of hESC-derived hepatocytes using small molecules (light grey bars) compared to growth factors (dark grey bars). Results are plotted relative to GAPDH. Data are presented as mean±sem. Asterisks indicate significant difference between gene expression in small molecule based and growth factor based maturation of hepatic progenitors (*p-value <0.1, **p-value <0.05). SM: hepatic precursors differentiated into hepatocytes using SB431542/DMSO; GF: hepatic precursors differentiated into hepatocytes using HGF and Follistatin. Thus.

In the third stage, SB431542, which is a TGFβ inhibitor, and DMSO were used to promote the differentiation of hepatic progenitors to hepatocytes. DMSO has been reported to promote generation of fetal liver cells but whether DMSO can direct hepatoblasts to hepatocytes without any tendency for cells to differentiate towards cholangiocytes is not well known. It has been shown that TGFβ signaling gradient promotes biliary differentiation. Therefore, the present inventors believed that a combination of DMSO and TGFβ inhibitor treatment will allow differentiation into hepatocytes and at the same time prevent differentiation into biliary lineage. After 8 days of treatment with SB431542 (TGFβ inhibitor) and DMSO, cells were characterized morphologically and expression of hepatocyte markers was analyzed by qPCR. By the end of the differentiation period, the small molecule differentiated hepatocyte-like cells showed characteristic hepatocyte morphology: polygonal in shape, large nuclei and granular cytoplasm (FIG. 11A). As known in the art, these characteristics have been observed in growth factor-differentiated hepatocyte like cells. The efficiency of hepatocyte differentiation was quantified using marker protein expression of Alb (FIG. 11B). Both small molecule-induced and growth factor-induced (6 days treatment with HGF and Follistatin) generation of hepatocytes showed comparable levels of Alb expression. Expression of Alb as well as other hepatic markers that have been previously been shown to be expressed at the second stage of differentiation (AFP, CK18 and HNF4α) were quantified using qPCR (FIG. 11C). The levels of these markers in the small molecule-differentiated cells were similar to growth factor-differentiated cells. In both approaches, decrease in levels of AFP and increase in levels of Alb, compared to the second stage of differentiation confirmed the differentiation of hepatocytes from the hepatic progenitors (FIGS. 11C and 10C). Furthermore, the cells also expressed hepatocyte markers alpha-1-antitrypsin (AAT), asialoglycoprotein receptor (ASGPR) and multidrug resistance protein 2 (MRP2), as well as cytochrome P450 enzymes, CYP3A4, CYP1A1 and CYP1A2 (FIG. 4B). The expression of ASGPR, CYP3A4, and CYP1A1 were similar in small molecule and growth factor-differentiated cells, while the expression of AAT, MRP2 and CYP1A2 was higher in the small molecule-differentiated cells. Adult liver expresses higher CYP1A2 and lower CYP1A1 compared to fetal liver cells and therefore a 9 fold increased expression of CYP1A2 in small molecule-matured cells might suggest that the small molecules are more efficient in generation of hepatic progenitors.

Hepatocytes generated using predominantly small molecules based approach are hereafter referred to as SM-Hep and hepatocytes generated using the growth factor approach are referred to as GF-Hep.

d. Functional Activity of hESC-Derived Hepatocytes

Figure 12:
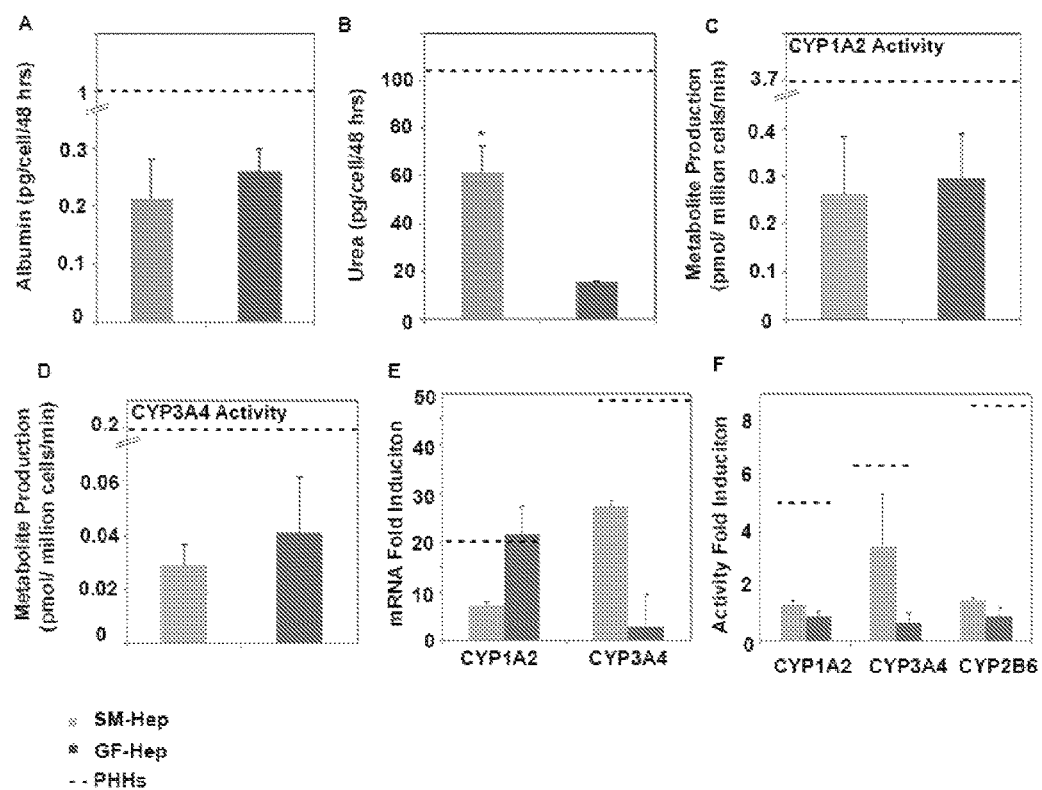
FIG. 12 shows the functional performance of hepatocytes derived from hESCs using small molecules (SM-Hep) and growth factors (GF-Hep) (A) Albumin, (B) Urea production (C) CYP1A2 and (D) CYP3A4 specific metabolite production by SM-Hep (light grey bars) and GF-Hep (dark grey bars). Cells were differentiated using either small molecules or growth factors for 20 days and supernatant was collected at day 20 for measuring albumin and urea production. Differentiated cells were treated with CYP1A2 and CYP3A4 specific substrates for quantifying metabolite production. The amount of albumin, urea and metabolite produced were normalized to cell numbers. Asterisks indicate significant difference between urea production in SM-Hep compared to GF-Hep (*p-value <0.05). (E) shows CYP1A2 and CYP3A4 induction in SM-Hep analyzed by gene expression. (F) shows CYP1A2, CYP3A4 and CYP2B6 induction analyzed by LC-MS. Data are presented as mean±sem. Functions were compared to levels in human primary hepatocytes obtained from 3 different donors (dotted lines). Thus.

To test whether the hepatocytes generated using the small molecule approach possess hepatocyte specific functions, albumin and urea production; CYP activity and induction of these cells were studied. The functions were compared to primary human hepatocytes (PHHs) data generated from three different hepatocyte donors. SM-Hep produced 0.21±0.067 pg/cell/48 hours albumin which was similar, to that of GF-Hep (FIG. 12A) and was about 20% of the level produced by primary human hepatocytes (PHHs). Urea production in SM-Hep was 62±11 pg/cell/48 hours which was significantly higher than that of GF-Hep (15±0.36 pg/cell/48 hours) and 57% of primary human hepatocytes (PHHs) (110 pg/cell/48 hours) (FIG. 12B). The activity levels of CYP enzymes in SM-Hep were compared to that of GF-Hep according to the metabolism of CYP1A2 and CYP3A4 substrates (FIG. 12C, D). The metabolite production by CYP1A2 for SM-Hep and GF-Hep was 0.26±0.12 and 0.30±0.091 pmol/million cells/min respectively. The metabolite production by CYP3A4 for SM-Hep and GF-Hep was 0.029±0.0074 and 0.041±0.020 pmol/million cells/min respectively. These values are about 8-10% of the metabolite production by primary human hepatocytes (PHHs) (3.75 pmol/million cells/min for CYP1A2 activity and 0.21 pmol/million cells/min for CYP3A4; average of 3 donors).

SM-Hep showed mRNA fold induction of 7±2.8 and 27±3.3 for CYP1A2 and CYP3A4 respectively (FIG. 12E). The fold induction of CYP1A2, although lower than GF-Hep (21±1.8 fold) for CYP1A2 was approximately 35% of primary human hepatocytes (PHHs) (PHHs fold induction=20; average of 3 donors, data known in the art). The fold induction for CYP3A4 was higher in the SM-Hep (27 fold±3.3) when compared to GF-Hep (2.8±1.8 fold) and was approximately 54% of primary human hepatocytes (PHHs) (PHHs fold induction=50; average of 3 lots). The fold inductions measured by mRNA levels were confirmed by functional activity (metabolite production in basal and induced samples were quantified by LCMS). GF-Hep showed low levels of CYP1A2, CYP3A4 and CYP2B6 induction (FIG. 12F). Induction levels for all three CYPs were higher in SM-Hep (approximately 1.5 fold for CYP1A2 and CYP2B6 and 3.5 fold for CYP3A4). Importantly, higher CYP3A4 induction observed in SM-Hep by gene expression analysis was confirmed by functional data. CYP1A2, CYP3A4 and CYP2B6 induction in primary human hepatocytes (PHHs) was 5.0, 6.2 and 8.9 respectively (average of 3 lots) and therefore SM-Hep showed approximately 30%, 56% and 17% induction for CYP1A2, CYP3A4 and CYP2B6 when compared to primary human hepatocytes (PHHs) respectively.

Taken together the results show that, the functional hepatocytes could be generated using the small molecule based differentiation approach.

e. Drug-Induced Toxicity of Differentiated Hepatocytes and Applications in Toxicity Screening To examine its applicability to drug screening, SM-Hep were treated with drugs that are known to cause hepatotoxicity (Table 2).

TABLE 2

$IC_{50}$ values for hepatotoxicity screening using hepatocytes differentiated using growth factors (GF) or small molecules (SM). $IC_{50}$ values were compared to primary human hepatocytes (PHHs).

| | $IC_{50}$(μm) | | | Statistical Significance | |
|---|---|---|---|---|---|
| | GF-Hep | SM-Hep | PH | p-value[a] | p-value[b] |
| Acetaminophen | $46.0 \times 10^3$ | $38.1 \times 10^3$ | $45.2 \times 10^3$ | >0.1 | 0.1 |
| Diclofenac | 1859.7 | 1927.7 | 3585.6 | >0.1 | >0.1 |
| Digoxin | 0.25 | 0.36 | 0.34 | >0.1 | >0.1 |
| Chlorpromazine | 61.3 | 66.9 | 71.8 | >0.1 | >0.1 |
| Quinidine | 538.5 | 728.2 | 562.9 | >0.1 | >0.1 |
| Troglitazone | 33.7 | 31.9 | 29.7 | >0.1 | >0.1 |

P-values[a] indicate significant statistical differences between $IC_{50}$ values in GF-Hep and SM-Hep.

P-values[b] indicate significant statistical differences between $IC_{50}$ values in SM-Hep and PHHs.

Figure 13:
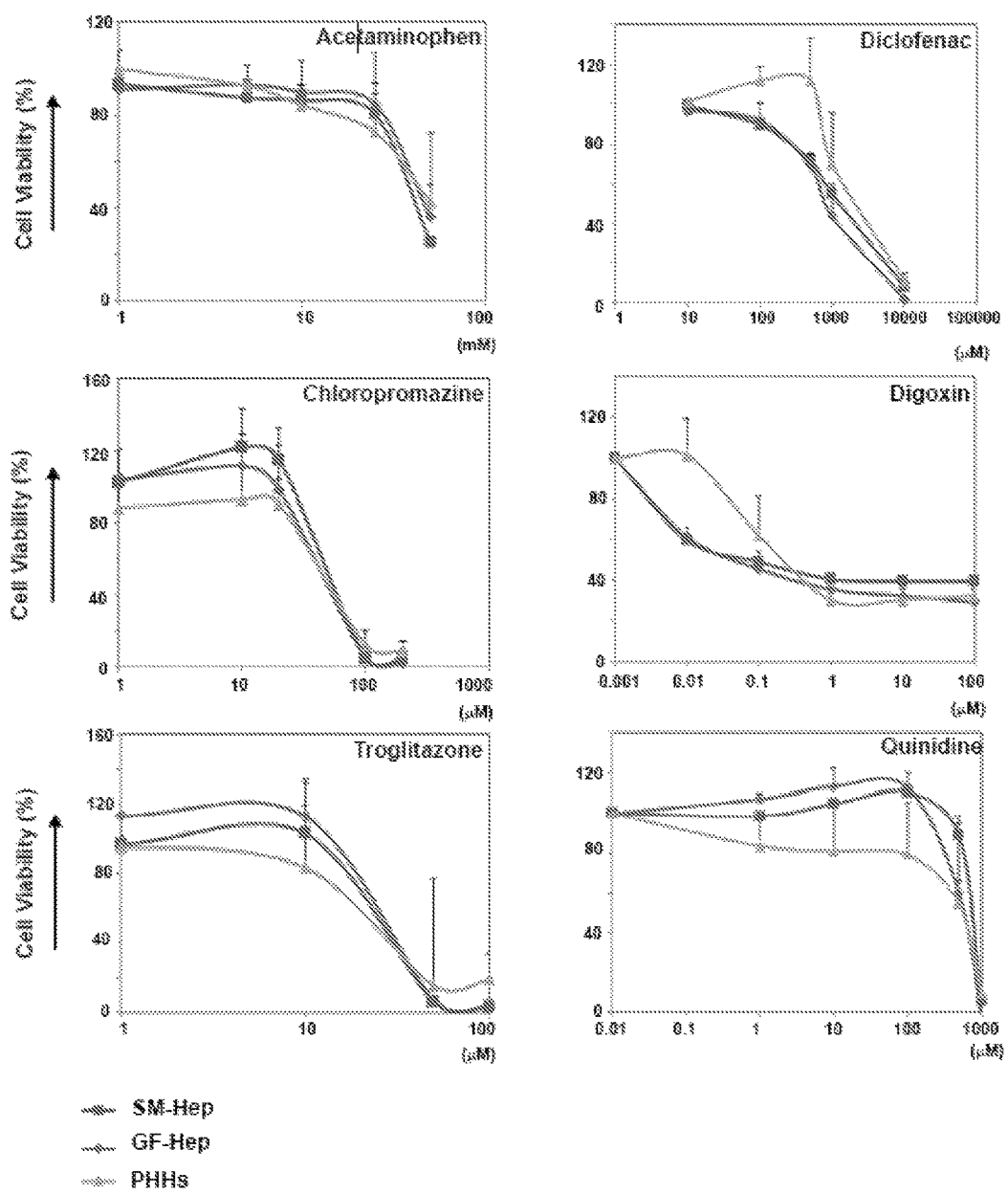
FIG. 13 shows the application of SM-Hep for drug testing. The cell viability of GF-Hep, SM-Hep and human primary hepatocytes (PHHs) was assessed by MTS assay after 24 hour exposure to different concentrations of test compounds. Cell viability is expressed as a percentage of cells treated with solvent alone. Data are presented as mean±sem. Thus.

These drugs included Acetaminophen, Diclofenac, Digoxin, Chlorpromazine, Quinidine and Troglitazone. Cell viability, assessed using MTT assay, was compared to GF-Hep as well as to primary human hepatocytes (PHHs). The results showed that the $IC_{50}$ values of GF-Hep and SM-Hep were comparable for all six drugs tested (FIG. 13). Both SM-Hep and GF-Hep showed very similar dose response curves with consistently similar $IC_{50}$, as shown in Table 2. There was no significant difference in the $IC_{50}$ of the drugs when GF-Hep and SM-Hep were compared (p-value[a], Table 2). This suggests that differentiation using a small-molecule based approach doesn't affect the sensitivity of the cells to paradigm hepatotoxicants. The susceptibility of the differentiated hepatocytes to the drugs to that of primary human hepatocytes (PHHs) were also compared. The drug-induced toxicity in differentiated hepatocytes (both SM-Hep and GF-Hep) was similar to that of the primary human hepatocytes (PHHs) when treated with all six drugs both in terms of the dose response curves and the $IC_{50}$ values (FIG. 13, Table 2). There was no statistically significant difference in the $IC_{50}$ of these drugs when SM-Hep and primary human hepatocytes (PHHs) were compared p-value[b] (Table 2). Thus, SM-Hep can serve as an alternative to primary hepatocytes for drug screening.

In one example, there is provided a protocol for the efficient differentiation of functional hepatocytes from hESCs. In one example, the protocol does not require the addition of recombinant growth factors except for Activin A.

In one example, the protocol has a second step. In one example, in the second step of the protocol, hepatic precursors were generated using sodium butyrate and DMSO.

In one example, the protocol has a third step. In one example, in the third step of the protocol, hepatic progenitor cells could be directed towards hepatocytes upon treatment with TGFβ inhibitor SB431542 and DMSO. In midphase fetal liver, TGFβ promotes liver progenitor cells to undergo biliary differentiation. In the present study, SB431542, in combination with DMSO, could be used to generate hepatocyte-like cells from their progenitor stage without the addition of growth factors. After 20 days of differentiation, the hepatocyte-like cells retained some immature characteristics, such as expression of AFP.

In one example, the SM-Hep generated in this study can be used for hepatotoxicity screening applications. In particular, since small molecules are cheaper and more stable than growth factors, SM-Hep would be cheaper compared to GF-Hep and especially to primary human hepatocytes (PHHs). In one example, the SM-Hep may be used in a pharmaceutical setting for drug testing where large scale screening of compounds would need hundreds of well plates and millions of cells. In one example, the SM-Hep may also be used to reduce batch to batch variability associated with different lots of growth factors and different lots of primary human hepatocytes (PHHs).

The invention claimed is:

1. A method of differentiating definitive endoderm in order to obtain hepatocyte, wherein the method comprises:
    a) subjecting definitive endoderm to at least one epigenetic modulator to obtain hepatoblasts,
    b) subjecting the hepatoblast to at least one stem cell differentiation pathway inhibitor to obtain hepatocyte;
    wherein steps a) and b) do not comprise the use of a growth factor;
    wherein before step a) the definitive endoderm is obtained by subjecting a stem cell to at least one compound which regulates stem cell differentiation by inhibiting kinase activity, wherein before step a) further comprises a growth factor for obtaining definitive endoderm, wherein the growth factor is Activin A;
    wherein at least two compounds which regulate stem cell differentiation by inhibiting kinase activity are used to obtain definitive endoderm, wherein one compound which regulates stem cell differentiation by inhibiting kinase activity is a phosphoinositide-3-kinase inhibitor; and
    wherein the method is performed for 20 days.

2. The method of claim 1, wherein the at least two compounds which regulate stem cell differentiation by inhibiting kinase activity are used to obtain definitive endoderm, wherein one compound is a glycogen synthase-3-kinase inhibitor.

3. The method of claim 1, wherein the at least two compounds which regulate stem cell differentiation by inhibiting kinase activity are used to obtain definitive endoderm, wherein one compound is a phosphoinositide-3-kinase inhibitor and a second compound is a glycogen synthase-3-kinase inhibitor.

4. The method of claim 1, wherein the compound which regulates stem cell differentiation by inhibiting kinase activity acts on the transforming growth factor beta (TGF-β) family/the SMAD signalling pathway/Activin and Wnt signalling pathways/phosphoinositide-3-kinase(PI3K)-AKT signalling pathway.

5. The method of claim 1, wherein the compound which regulates stem cell differentiation by inhibiting kinase activity is selected from the group consisting of 2-Morpholin-4-yl-8-phenylchromen-4-one (LY294002), (1alpha,11alpha)-11-(Acetyloxy)-1-(methoxymethyl)-2-oxaandrosta-5,8-dieno(6,5,4-bc)furan-3,7,17-trione (Wortmannin), (1E,4S,4aR,5R,6aS,9aR)-5-(acetyloxy)-1-[(di-2-propen-1-ylamino)methylene]-4,4a,5,6,6a,8,9,9a-octahydro-11- hydroxy-4-(methoxymethyl)-4a,6a-dimethyl-cyclopenta[5,6]naphtho[1,2-c]pyran-2,7,10(1H)-trione (PX-866), (8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate (SF1126), 3-[4-(4-morpholinyl)pyrido[3',2',:4,5]furo[3,2-d]pyrimidin-2-yl]-phenol (PI-103), 2-(1H-indazol-4-yl)-6-(4-methanesulfonyl-piperazin-1-ylmethyl)-4-morpholinyl-4-yl-thieno[3,2-d]pyrimidine (GDC-0941), 4-[2,3-dihydro-3-methyl-2-oxo-8-(3-quinolinyl)-1H-imidazo[4,5-c]quinolin-1-yl]-α,α-dimethyl-benzeneacetonitrile (NVP-BEZ235), (S)-1-(4-((2-(2-aminopyrimidin-5-yl)-7-methyl-4-morphlinothieno[3,2-d]pyrimidin-6-yl)methyl)piperazin-1-yl)-2-hydroxypropan-1-one (GDC-0980), 2-amino-8-ethyl-4-methyl-6-(1H-pyrazol-3-yl)pyrido[2,3-d]pyrimidin-7(8H)-one (SAR245409, XL-765), 2,4-Difluoro-N-{2-(methyloxy)-5-[4-(4-pyridazinyl)-6-quinolinyl]-3-pyridinyl}benzenesulfonamide (GSK2126458), 1-(4-(4-(dimethylamino)piperidine-1-carbonyl)phenyl)-3-(4-(4,6-dimorpholino-1,3,5-triazin-2-yl)phenyl)urea (PKI-587/PF-05212384), 2-amino-8-[trans-4-(2-hydroxyethoxy)cyclohexyl]-6-(6-methoxy-3-pyridinyl)-4-methyl-pyrido[2,3-d]pyrimidin-7(8H)-one (PF-04691502), glycogen synthase-3-kinase inhibitors, phosphoinositide-3-kinase inhibitors and 6-bromoindirubin-3'-oxime (BIO).

6. The method of claim 1, wherein the stem cell differentiation pathway inhibitors affect at least one differentiation pathway selected from the group consisting of Notch pathway, bone morphogenic proteins (BMP) pathway, fibroblast growth factor (FGF) pathway and transforming growth factor beta (TGFβ) pathway.

7. The method of claim 6, wherein the stem cell differentiation pathway inhibitor is a transforming growth factor beta inhibitor (TGF-β inhibitor).

8. The method of claim 1, wherein the epigenetic modulator is a histone modification agent selected from a group consisting of histone deacetylases and histone deacetylase inhibitors (HDACi).

9. The method of claim 1, wherein the concentration of the epigenetic modulator in step a) is lower than the at least one stem cell differentiation pathway inhibitor in step b).

10. The method of claim 8, wherein the histone deacetylase inhibitor is selected from a group consisting of sodium butyrate and DMSO.

11. The method of claim 1, wherein step a) comprises two epigenetic modulators.

12. The method of claim 1, wherein step b) comprises two stem cell differentiation pathway inhibitors.

13. The method of claim 1, wherein step b) comprises a stem cell differentiation pathway inhibitor and an epigenetic modulator.

14. The method of claim 1, further comprising performing a drug screening, wherein performing the drug screening comprises subjecting the hepatocyte to a test sample and measuring the viability of the hepatocyte and/or measuring the functional phenotype of the hepatocyte.

15. The method of claim 14, wherein the drug screening is for an application selected from a group consisting of drug toxicity screening, drug cytotoxicity assessment cell therapy, tissue engineering and tissue regeneration.

* * * * *